(12) United States Patent
Backs et al.

(10) Patent No.: US 7,863,414 B2
(45) Date of Patent: Jan. 4, 2011

(54) METHODS OF TREATMENT AND USES FOR CAMKII AND ITS INTERACTION WITH HDACS AND CALPAIN

(75) Inventors: Johannes Backs, Dallas, TX (US); Brooke Harrison, Longmont, CO (US); Khai Huynh, Westminster, CO (US); Keith Koch, Erie, CO (US); Timothy A. McKinsey, Broomfield, CO (US); Eric Olson, Dallas, TX (US); Nikos Pagratis, Boulder, CO (US)

(73) Assignees: The Board of Regents of the University of Texas Systems, Austin, TX (US); Gilead Sciences, Inc., Foster City, CA (US)

( * ) Notice: Subject to any disclaimer, the term of this patent is extended or adjusted under 35 U.S.C. 154(b) by 322 days.

(21) Appl. No.: 11/560,950

(22) Filed: Nov. 17, 2006

(65) Prior Publication Data

US 2007/0142285 A1 Jun. 21, 2007

Related U.S. Application Data

(60) Provisional application No. 60/737,952, filed on Nov. 18, 2005.

(51) Int. Cl.
*A61K 38/04* (2006.01)
(52) U.S. Cl. .................. 530/324; 530/300; 530/325; 530/326; 530/327; 530/328; 530/329; 530/330; 514/2
(58) Field of Classification Search .................. 514/2; 530/324, 300, 325–330
See application file for complete search history.

(56) References Cited

U.S. PATENT DOCUMENTS

| 6,706,686 B2 | 3/2004 | Long et al. ............ 514/10 |
| 6,706,886 B2 | 3/2004 | van Deyn ............ 548/240 |
| 6,946,441 B2 | 9/2005 | Long ............ 514/10 |

OTHER PUBLICATIONS

Chang et al., "Histone deacetylases 5 and 9 govern responsiveness of the heart to a subset of stress signals and play redundant roles in heart development," *Mol. Cell. Biol.*, 24:8467-76, 2004.
Colomer & Means, "Chronic elevation of calmodulin in the ventricles of transgenic mice increases the autonomous activity of calmodulin-dependent protein kinase II, which regulates atrial natriuretic factor gene expression," *Mol. Endocrinol.*, 14:1125-1136, 2000.
Colomer et al., "Pressure overload selectively up-regulates $Ca^{2+}$/calmodulin-dependent protein kinase II in vivo," *Mol. Endocrinol.*, 17:183-92, 2003.
Davis et al., "Calcium/calmodulin-dependent protein kinase activates serum response factor transcription activity by its dissociation from histone deacetylase, HDAC4," *J. Biol. Chem.*, 278:20047-58, 2003.
Dequiedt et al., "Phosphorylation of histone deacetylase 7 by protein kinase D mediates T cell recepto-induced Nur77 expression and apoptosis," *J. Exp. Med.*, 201:793-804, 2005.
Frey & Olson, "Cardiac hypertrophy: The good, the bad, and the ugly," *Annu. Rev. Physiol.*, 65:45-79, 2003.
Gusterson et al., "The transcriptional co-activators CREB-binding protein (CBP) and p300 play a critical role in cardiac hypertrophy that is dependent on their histone acetyltransferase activity," *J. Biol. Chem.*, 278:6838-47, 2003.
Hoch et al., "Identification and expression of δ-isoforms of the multifunctional $Ca^{2+}$/calmodulin-dependent protein kinase in failing and nonfailing human myocardium," *Circ. Res.*, 84:713-21, 1999.
Kao et al., "Mechanism for nucleocytoplasmic shuttling of histone deacetylase 7," *J. Biol. Chem.*, 276:47496-507, 2001.
Kato et al., "Calmodulin kinases II and IV and calcineurin are involved in leukemia inhibitory factor-induced cardiac hypertrophy in rats," *Circ. Res.*, 87:937-45, 2000.
Kirsh et al., "The SUMO E3 ligase RanBP2 promotes modification of the HDAC4 deactylase," *Embo. J.*, 21:2682-91, 2002.
McKinsey & Olson, "Cardiac histone acetylation—therapeutic opportunities abound," *Trends Genet.*, 20:206-13, 2004.
McKinsey and Olson, "Toward transcriptional therapies for the failing heart: chemical screens to modulate genes," *J Clin Invest*, 115:538-46, 2005.
McKinsey et al., "Identification of a signal-responsive nuclear export sequence in class II histone deacetylases," *Mol .Cell. Biol.*, 21:6312-21, 2001.

(Continued)

*Primary Examiner*—David Lukton
(74) *Attorney, Agent, or Firm*—Fulbright & Jaworski

(57) ABSTRACT

The present invention provides for methods of treating and cardiac hypertrophy, heart failure, dilated cardiomyopathy or hypertension comprising the use of CaMKII-HDAC binding domains. The present invention discloses not only the fact that CaMKII binds to HDAC4 at a specific site, but that HDAC4 may dimerize with other HDACs. Both events can lead to export of HDACs from the nucleus to the cytoplasm, an event associated with the development of heart disease. Thus the methods of treatment and the screening methods of the present invention are novel attempts to prevent, treat or identify therapies for cardiac hypertrophy, heart failure, dilated cardiomyopathy or hypertension.

9 Claims, 13 Drawing Sheets

OTHER PUBLICATIONS

McKinsey et al., "Signal-dependent nuclear export of a histone deacetylase regulates muscle differentiation," *Nature*, 408:106-111, 2000.

McKinsey et al., "Activation of a myocyte enhancer factor-2 transcription factor by calcium/calmodulin-dependent protein kinase-stimulated binding of 14-3-3 to histone dacetylase 5," *Proc. Natl. Acad. Sci. USA*, 97:14400-14405, 2000.

Miska et al., "HDAC4 deacetylase associates with and represses the MEF2 transcription factor," *Embo. J.*, 18:5099-107, 1999.

Miyano et al., "Purification and characterization of a brain-specific multifunctional calmodulin-dependent protein kinase from rat cerebellum," *J. Biol. Chem.*, 267:1198-203, 1992.

Parra et al., "Protein kinase D1 phosphorylates HDAC7 and induces its nublear export after t-cell receptor activation," *J. Biol. Chem.*, 280:13762-70, 2005.

Ramirez et al., "The nuclear $\delta_B$ of $Ca^{2+}$/calmodulin-dependent protein kinase II regulates atrial natriuretic factor gene expression in ventricular myocytes," *J. Biol. Chem.*, 272:31203-8, 1997.

Uemura et al., "Demenstration of a $Ca^{2+}$/calmodulin-dependent protein kinase cascade in the hog heart," *Biochem. Biophys. Res. Commun.*, 249:355-60, 1998.

Vega et al., "Protein kinases C and D mediate agonist-dependent cardiac hypertrophy through nuclear export of histone deacetylase 5," *Mol. Cell. Biol.*, 24:8374-85, 2004.

Yanazume et al., "Cardiac p300 is involved in myocyte growth with decompensated heart failure," *Mol. Cell. Biol.*, 23:3593-606, 2003.

Zhang et al., "Class II histone deacetylases act as signal responsive repressors of cardiac hypertrophy," *Cell*, 110:479-88, 2002.

Zhang et al., "The $\delta_c$ isoform of CaMKII is activated in cardiac hypertrophy and induces dilated cardiomyopathy and heart failure," *Circ. Res.*, 92:912-9, 2003.

Zhang et al., "Calmodulin kinase II inhibition protects against structural heart disease," *Nat. Med.*, 2005.

"Selective enzyme interaction contributes to cardiac hypertrophy," *Medical News Today*, http://www.medicalnewstoday.com/medicalnews.php?newsid=44911, Jun. 11, 2006.

Backs and Olson, "Histone Deacetylase 4 serves as a target of CaM Kinase II-dependent regulation of cardiomyocyte growth," *ELSO 2005 Poster Abstracts*, http://www.elso.org/index.php?id=abstrlist2005&lid=68&symp=4, Sep. 5, 2005.

Backs et al., "CaM kinase II selectively signals to histone deacetylase 4 during cardiomyocyte hypertrophy," *J. Clin. Invest.*, 116:1853-1864, 2006.

Little et al., "Nuclear calcium/calmodulin-dependent protein kinase IIdelta preferentially transmits signals to histone deacetylase 4 in cardiac cells," *J. Biol. Chem.*, 282:7219-7231, 2007.

PCT International Search Report and Written Opinion, issued in International Application No. PCT/US2006/061038, dated Nov. 16, 2007.

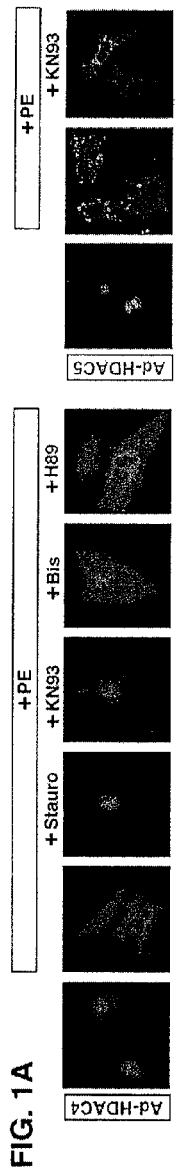
FIG. 1A
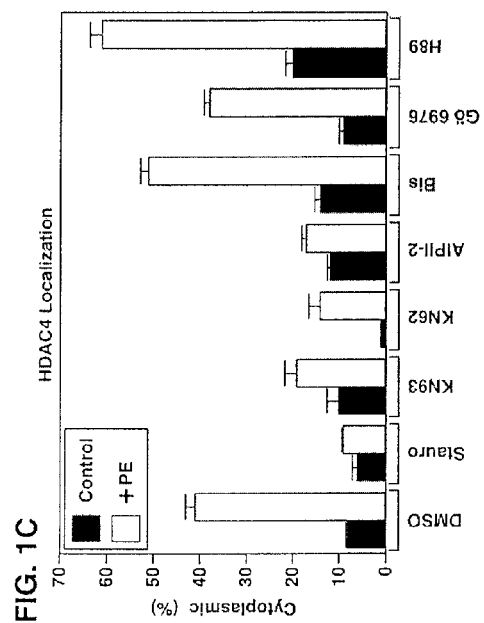
FIG. 1B
FIG. 1C
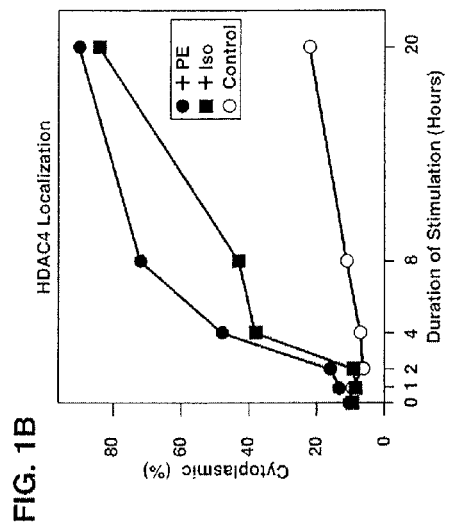
Fig. 1D
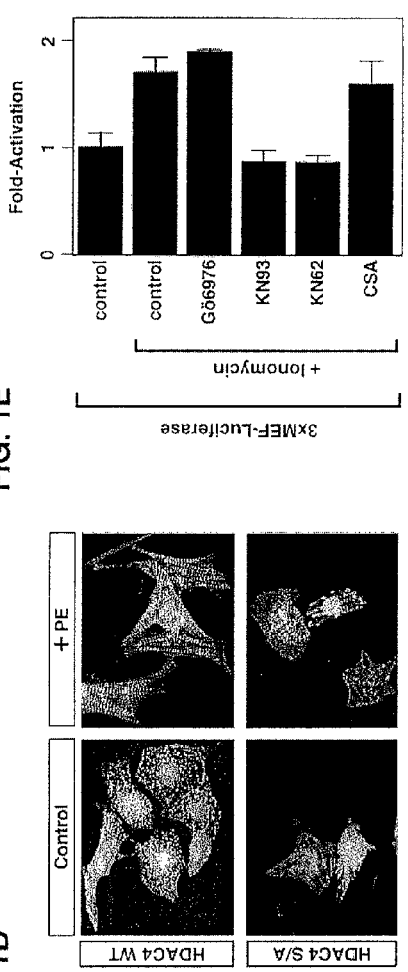
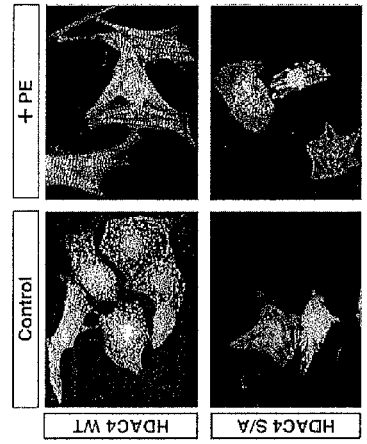
FIG. 1E

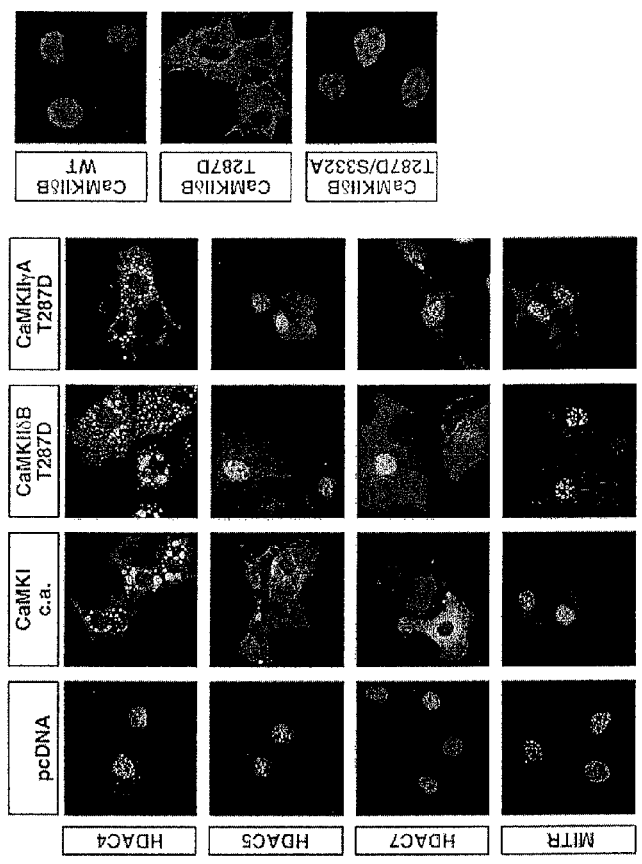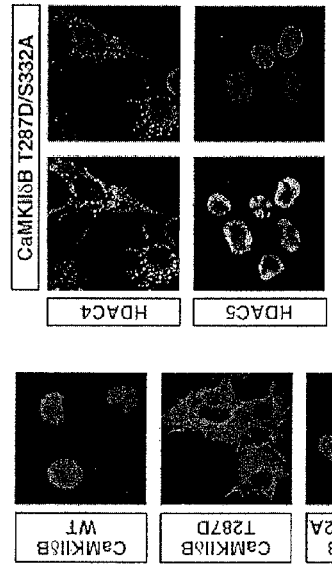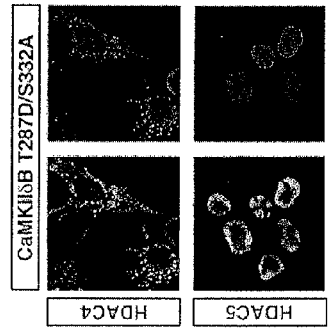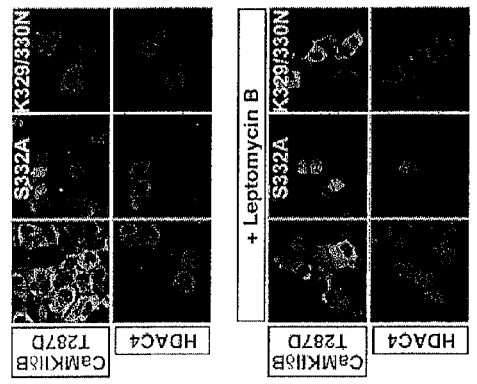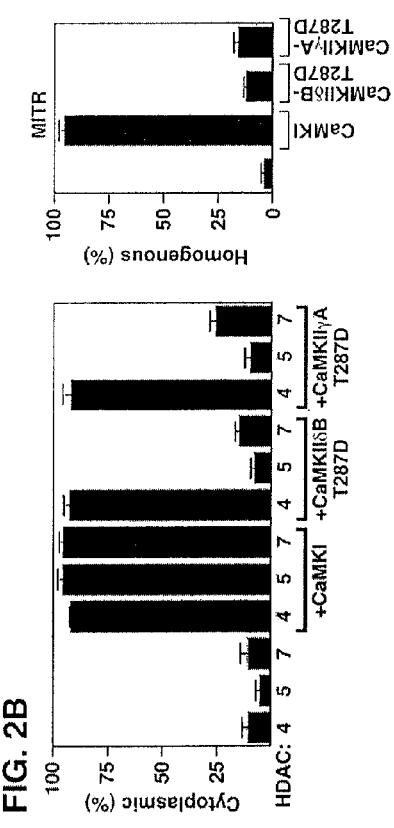

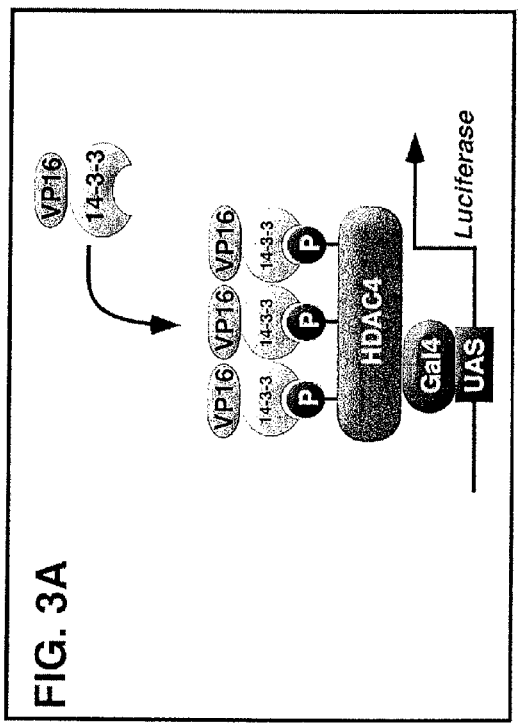
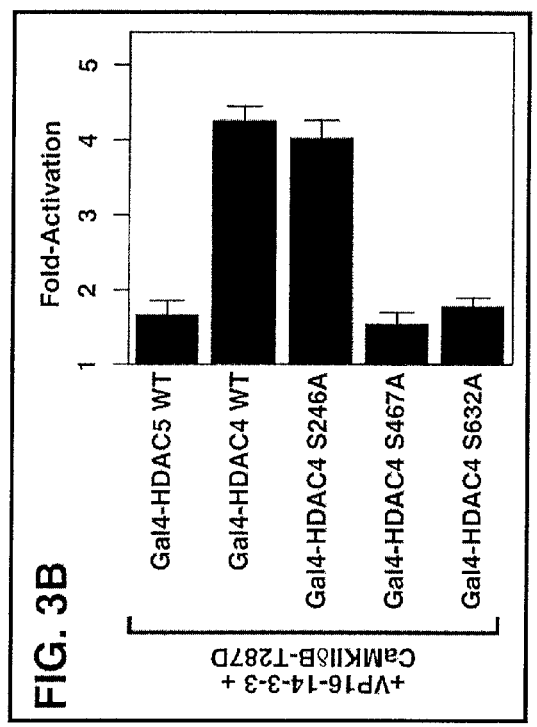
FIG. 3A
FIG. 3B

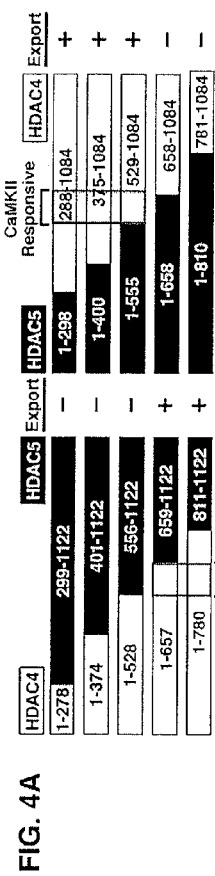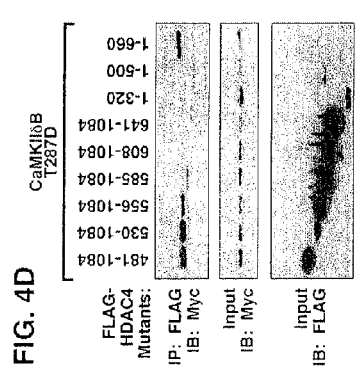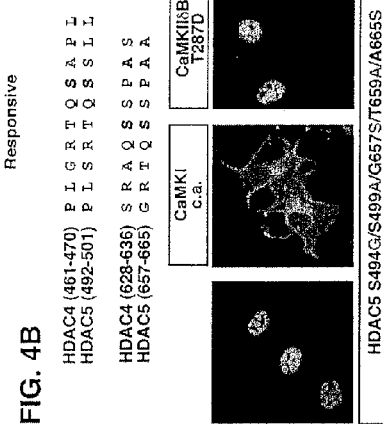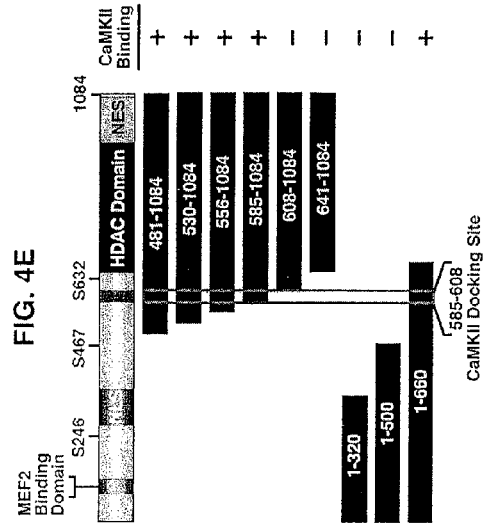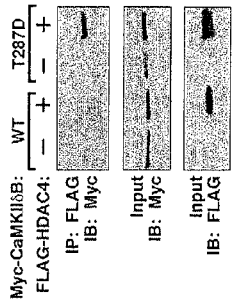
FIG. 4A
FIG. 4B
FIG. 4D
FIG. 4E
FIG. 4C

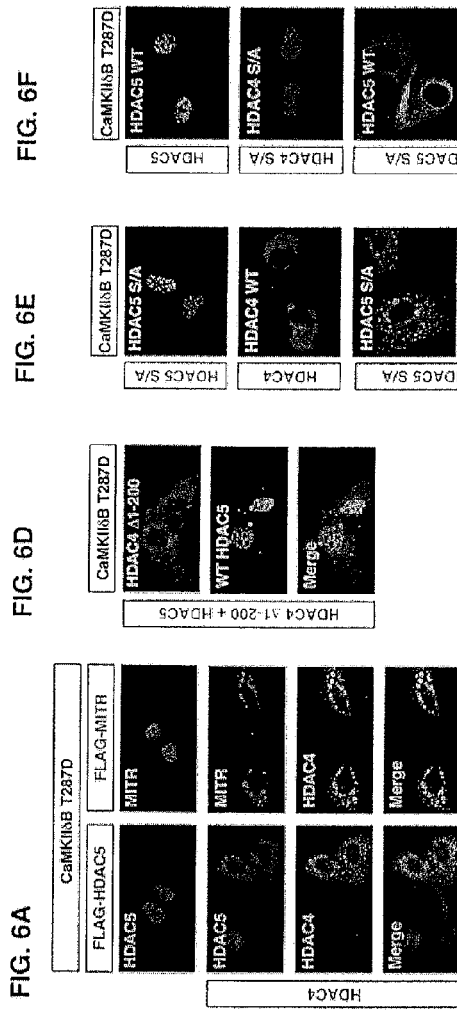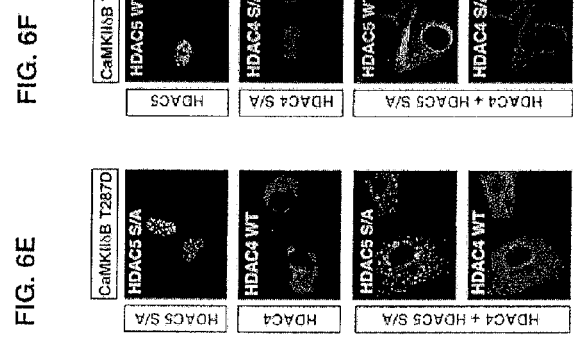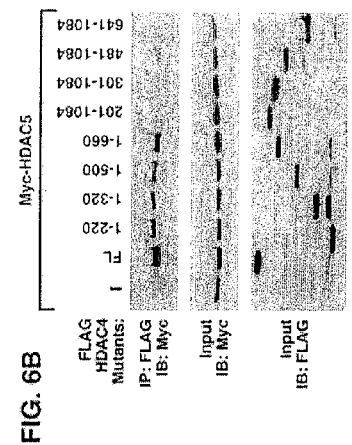

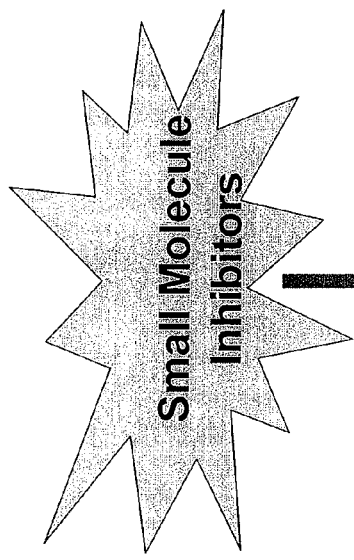
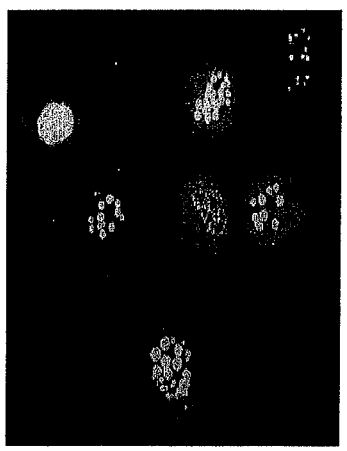
FIG. 10

FIG. 11
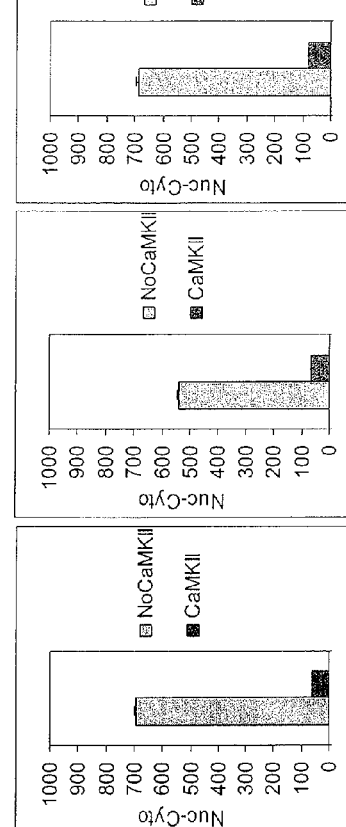
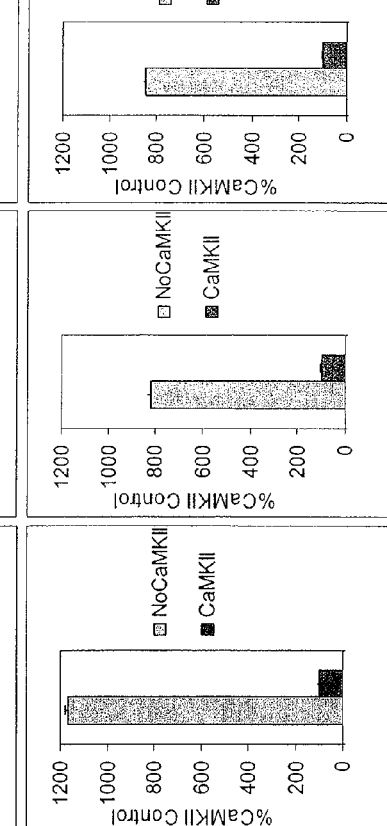

METHODS OF TREATMENT AND USES FOR CAMKII AND ITS INTERACTION WITH HDACS AND CALPAIN

The present invention claims benefit of priority to U.S. Provisional Application Ser. No. 60/737,952, filed Nov. 18, 2005, the entire contents of which are hereby incorporated by reference.

The government owns rights in this application pursuant to federal funding from the National Institutes of Health under Grant No. R01 HL53351-06.

BACKGROUND OF THE INVENTION

1. Field of the Invention

The present invention relates generally to the fields of biology, cardiology, physiology and molecular biology. More particularly, it concerns cardiovascular disease and hypertension. Specifically, the invention relates to the use of the Calcium-Calmodulin Kinase II (CaMKII) binding domain with histone deactylase (HDAC) 4, as well as the use of the HDAC dimerization domain, to treat or prevent cardiovascular diseases and hypertension, or to screen for compounds that could be used to treat or prevent cardiovascular diseases and hypertension.

2. Description of Related Art

Hypertension, a highly underdiagnosed problem in the world today, is a frequent precursor of a myriad of syndromes including cardiac hypertrophy, many renal diseases, and congestive heart failure. Uncontrolled or undiagnosed high blood pressure, or hypertension, can be basically described as the force of blood against the artery walls being too strong. High blood pressure can damage the arteries, heart, and kidneys, and lead to atherosclerosis and stroke. Hypertension is called a "silent killer" because it does not cause symptoms unless it is severely high and causes major organ damage if not treated.

Heart failure, cardiac hypertrophy and other cardiovascular diseases can occur as a result of hypertension or can lead to the development of hypertension, and the symptoms manifested may include the left ventricle being hypertrophied and dilated, left ventricular diastolic dysfunction, and indices of systolic function, such as ejection fraction, being reduced. Untreated high blood pressure can also damage the delicate lining of the blood vessels. Once damaged, fat and calcium can easily build up along the artery wall, forming a plaque. The blood vessel becomes narrowed and stiff (atherosclerosis), and blood flow through the blood vessel is reduced. Over time, decreased blood flow to certain organs in the body can cause damage, leading to a variety of diseases such as heart disease, heart attack, abnormal heartbeat, stroke, kidney (renal) failure, peripheral arterial disease, and eye damage (retinopathy).

Signaling by CaMKII has been implicated in such pathological cardiac growth, but the downstream effectors of CaMKII action remain poorly defined. CaM kinases have, however, been shown to interact with and modulate signaling through the HDAC/myocyte enhancer factor-2 family (MEF2) cascade (Davis et al., 2003). MEF2's are a family of transcription factors that interact with HDACs and they have been previously implicated in cardiovascular diseases, especially those diseases associated with abnormal intracellular calcium levels (like those which were initially found to involve CaMKII's). For example, a variety of stimuli can elevate intracellular calcium, resulting in a cascade of intracellular signaling systems or pathways, including calcineurin, CaM kinases, PKC and MAP kinases. All of these signals activate MEF2 and can result in activation of an unwanted gene program known as the fetal gene program. However, it is still not completely understood how the various signal systems exert their effects on MEF2 and modulate its signaling. In work attempting to understand MEF2 and cardiovascular disease, it was shown that certain HDACs are involved in modulating MEF2 activity (McKinsey et al., 2000) and it has been previously shown by the inventors that HDACs are intimately involved in regulation of cardiac gene expression (McKinsey & Olson, 2004).

Seventeen different HDACs have been cloned from vertebrate organisms and have been separated into three different classes. All share homology in the catalytic region. Histone acetylases (HATs) and deacetylases play a major role in the control of gene expression. The balance between activities of HATs, and HDACs determines the level of histone acetylation and further, gene expression. Acetylated histones cause relaxation of chromatin and activation of gene transcription, whereas deacetylated chromatin is generally transcriptionally inactive. HDAC4 and 5, for example, have now been shown to dimerize with MEF2 and repress the transcriptional activity of MEF2, which can be beneficial to the heart and the peripheral vasculature (McKinsey et al., 2000).

Years of research have also highlighted the important role of HDACs in cancer biology, demonstrating a role for HDACs in a diversity of disease settings. In fact, various inhibitors of HDACs are being tested in the clinic for their ability to induce cellular differentiation and/or apoptosis in cancer cells (Marks et al., 2000). Such inhibitors include suberoylanilide hydroxamic acid (SAHA) (Butler et al., 2000; Marks et al., 2001); m-carboxycinnamic acid bis-hydroxamide (Coffey et al., 2001); and pyroxamide (Butler et al., 2001). These studies were initially summarized as indicating "that the hydroxamic acid-based HPCs, in particular SAHA and pyroxamide—are potent inhibitors of HDAC in vitro and in vivo and induce growth arrest, differentiation, or apoptotic cell death of transformed cells . . . [and thus] are lead compounds among the family of hydroxamic acid-based HPCs and are currently in phase I clinical trials" (Marks et al., 2000). Since that time, a multitude of companies have initiated research programs into the anti-tumor effects of HDAC inhibitors. More on point, HDAC inhibitors have been shown to be anti-hypertrophic and capable of treating heart failure (U.S. Pat. No. 6,706,886 and U.S. patent application Ser. No. 10/801,985, hereinafter incorporated in their entirety by reference). To date, however, no therapeutic approach for cardiovascular disease has supplanted the need for newer or better therapies.

SUMMARY OF THE INVENTION

Thus, and in accordance with the present invention, there is provided a method of treating or preventing cardiac hypertrophy, heart failure, dilated cardiomyopathy, arrhythmias or hypertension comprising (a) identifying a subject suffering from or at risk of suffering from cardiac hypertrophy, heart failure, dilated cardiomyopathy, arrhythmias or hypertension; and (b) administering to said patient an agent that specifically inhibits the interaction between a class II Histone Deacetylase (HDAC) and Calcium/Calmodulin Kinase II (CaMKII). The agent used may be a peptide, and the peptide may be an HDAC4 peptide, and in specific embodiments it comprises the docking site to CaMKII, or more particularly it may only comprise the docking site and may be 5 amino acids in length or longer. In other embodiments, said peptide is a peptide of CaMKII comprising the docking site to class II HDACs. In specific embodiments, it is a peptide of CaMK-II α, β, δ, or γ comprising the docking site to class II HDACs, and in other embodiments the peptide consists of only the HDAC4/CaMKII docking site and may be 5 amino acids in length or longer.

In another embodiment, there is provided a method of treating or preventing cardiac hypertrophy, heart failure, dilated cardiomyopathy or hypertension comprising (a) identifying a subject suffering from or at risk of suffering from cardiac hypertrophy, heart failure, dilated cardiomyopathy, arrhythmias or hypertension comprising; and (b) administering to said patient an agent that specifically inhibits the dimerization of class II HDACs. In certain embodiments, the agent may be a peptide, and in particular a class II HDAC peptide. In specific embodiments, this peptide comprises the dimerization region of class II HDACs, and in additional contemplated embodiments, the peptide is an HDAC4 peptide. In certain embodiments, the aforementioned class II HDAC peptide specifically interacts with HDAC4.

In yet another embodiment, there is provided a method for identifying a compound that could be used to inhibit the peptidic or proteolytic activity of calpain by (a) providing a peptide generated from CaMKII that contains the calpain cleavage site, (b) labeling the peptide with an agent that allows for downstream measurement of calpain cleavage, (c) mixing the peptide with calpain and a compound of interest; and (d) comparing the cleavage of the peptide in the presence of compound as compared to calpain mediated cleavage without compound; wherein decreased cleavage of the peptide by calpain in the presence of the compound as compared to cleavage without compound identifies the compound as a compound that could be used to treat or prevent cardiac hypertrophy, heart failure, dilated cardiomyopathy or hypertension. In specific embodiments, of the invention the peptide is generated from CaMKII α, β, δ, or γ, and more specifically the CaMKII is CaMKII-δb (hereinafter "Calcium/Calmodulin Kinase II delta b" may be referred to as CaMKIIdb, CaMKIIδb, or CaMKIIδB). In other specific embodiments the calpain is m-calpain or μ-calpain. The peptide may be labeled with a phosphoryl group and a fluorescent dye. In certain embodiments, comparing the cleavage of said peptide by calpain comprises the use of fluorescence resonance energy transfer (FRET), and in other embodiments said peptide is coupled to amino-4-methylcoumarin (AMC).

In yet another embodiment, there is provided a method for identifying a compound capable of disrupting the interaction between CaMKIIδb and HDAC comprising (a) providing a CaMKIIδb protein labeled with a first agent and a HDAC protein labeled with a second agent, wherein each protein is either directly or indirectly labeled, and further wherein said first agent emits a measurable signal when in proximity of said second agent, (b) mixing said proteins in a solution, and (c) adding a compound of interest to the mixture and comparing the signal; wherein a decrease in the measured signal as compared to the signal without compound identifies the compound as a compound that inhibits this interaction. In specific embodiments, the CaMKIIδb and HDAC are purified, and they may be purified from a human or a rodent. In other embodiments, HDAC is HDAC4. In other embodiments, the first and second agents used are labeled antibodies wherein the antibody to CaMKIIδb is labeled with a different agent than the antibody to HDAC. In yet additional embodiments, the method further comprises the use of a labeled secondary antibody that recognizes the primary antibody to CaMKIIδb and another labeled secondary antibody that recognizes the primary antibody to HDAC, wherein each secondary antibody is labeled with a different agent. The label used on the primary antibody may be a fluorescent molecule such as fluorescein, rhodamine, Europium, Samarium, Terbium, or allophycocyanin; and the secondary antibody may be labeled with a fluorescent molecule such as fluorescein, rhodamine, Europium, Samarium, Terbium, or allophycocyanin. In other embodiments, either agent may be a scintillation proximity (SPA) bead and or a radionuclide. In other embodiments, it is contemplated that indirect labeling comprises the use of chemiluminescent donor and acceptor beads, wherein only one protein is labeled and wherein fluorescent polarization (FP) is used to measure the signal. Alternatively, it is also contemplated that a secondary assay may be used to measure the signal, and said secondary assay may be an enzyme linked immunosorbent assay (ELISA), wherein said ELISA utilizes a lanthanide chelate conjugated secondary antibody.

In a further embodiment, there is provided a method of screening for anti-hypertrophic compounds capable of inhibiting the nuclear export of HDAC as mediated by CaMKIIδb that could be used to treat or prevent cardiac hypertrophy, heart failure, dilated cardiomyopathy or hypertension comprising (a) transfecting or infecting cells with a vector that expresses a tagged and activated HDAC protein and with a vector that expresses an activated CaMKIIδb, (b) adding a compound of interest to the cells, and (c) measuring the amount of HDAC located in the nucleus and cytoplasm of cells exposed to the agent as opposed to cells left untreated; wherein an increase in the amount of HDAC found in the nucleus as compared to the amount found in the cytoplasm of untreated cells identifies the compound as an anti-hypertrophic compound. In specific embodiments, the HDAC is HDAC4, and in additional embodiments the tagged HDAC protein is tagged at the carboxy-terminus with GFP, myc, HA, flag, or 6histidine. In other embodiments, the activated CaMKIIδb contains a mutation at position 287 from threonine to aspartic acid. Finally, it is contemplated that said measuring comprises fluorescent microscopy.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-E—Nuclear export of HDAC4 in cardiomyocytes. NRVMs were infected with adenoviral Flag-HDAC4 or GFP-HDAC5. Subcellular distribution of HDAC4 and 5 was verified following stimulation with phenylephrine (PE; 20 mmol/l) or isoprenaline (Iso; 10 μmol/l) for 4 hrs. As indicated, NRVMs were pre-treated with the kinase inhibitors staurosporine (Stauro; 500 nmol/l), KN93 (5 μmol/l), KN62 (10 μmol/l), autoctamide-2 related inhibitory peptide II (AIPII-2; 500 nmol/l), bisindolylmaleimide I (Bis; 2.5 μmol/l), Gö6976 (200 nmol/l) or H89 (1 μmol/l). Treatment with PE and Iso time-dependently induced nuclear export of HDAC4. Only the general serine/threonine-kinase inhibitor Stauro and the CaMKII inhibitors KN93, KN62 and AIPII-2 were effective in blocking HDAC4 nuclear export in response to PE. HDAC5 was also exported in response to PE but this was not blocked by CaMKII inhibition with KN93. (FIG. 1A) Representative images. (FIG. 1B) Quantitative analysis of time-dependent PE- and Iso-induced nuclear export of HDAC4. (FIG. 1C) Effects of kinase inhibitors on PE-induced nuclear export of HDAC4. (FIG. 1D) NRVMs were infected with adenoviruses encoding wild-type Flag-HDAC4 (wt) or a mutant lacking the phosphorylation sites Ser-246, -467 and -632 (HDAC4 S/A). One day after transfection, cells were serum-starved for 24 h and then stimulated with PE (20 µmol/l) for another 24 h. In contrast to HDAC4 wt, HDAC4 S/A was refractory to PE-induced nuclear export and blocked the hypertrophic response (sarcomeric organization, as assessed by immunostaining for sarcomeric α-actinin; green). Anti-Flag staining is visualized in red. (FIG. 1E) Reporter assay of endogenous MEF2 activity. NRVMs were transfected with a MEF2-dependent luciferase reporter harboring three MEF2 DNA-binding sites (3xMEF2-Luc) and a CMV-driven beta-galactosidase reporter construct to control for transfection efficiency. One day after transfection, cells were serum-starved for 24 h and then stimulated with ionomycin (0.25 µmol/l) for 16 h. As indicated, NRVMs were pretreated with the PKD inhibitor Gö6976 (200 nmol/l), the CaMKII inhibitors KN93 (2.5 µmol/l) and KN62 (5 µmol/l) and the calcineurin inhibitor cyclosporine A (CSA; 1 µmol/l). Only CaMKII inhibitors were effective in blocking the ionomycin-induced increase of endogenous MEF2 activity.

FIGS. 2A-E—Selective response of HDAC4 to CaMKII and regulation of CaMKII subcellular localization. Cos cells were transfected with GFP-HDAC4, GFP-HDAC5, Flag-HDAC7 or GFP-MITR together with either an empty vector (pcDNA), constitutively active CaMKI (c.a.), CaMKIIδB (T287D) or CaMKIIγA (T287D). CaMKI c.a. induced nuclear export of all HDACs and changed the predominant nuclear localization of MITR from punctate to homogenous. CaMKIIδB-T287D and CaMKIIγA-T287D selectively induced nuclear export of HDAC4 but did not affect the subcellular distribution of HDAC5, 7 and MITR. (FIG. 2A) Representative images. (FIG. 2B) Quantitative analysis. (FIG. 2C) Cos cells were transfected with wild-type (wt), constitutively active (T287D) and a CaMKIIδB mutant carrying two point mutations (T287D/S332A). In contrast to the wild-type kinase, CaMKIIδB-T287D localized predominantly to the cytosol. Substitution of Ser-332 rendered CaMKIIδB-T287D constitutively active and nuclear. (FIG. 2D) Cos cells were co-transfected with CaMKIIδB-T287D/S332A and HDAC4 or HDAC5. Note, that only HDAC4 was exported in response to the double CaMKIIδB mutant and co-localized with the kinase. (FIG. 2E) Cos cells were first transfected with the indicated CaMKIIδB mutants and 12 hours later with HDAC4. Four hours after transfection with HDAC4, cells were treated for another 12 hours either with leptomycin B (lower panel) or the vehicle ethanol (upper panel). Note that HDAC4 only accumulates in the nucleus in the presence of the constitutive nuclear and active mutant (CaMKIIδB T287D/S332A), but not in the presence of CaMKIIδB T287D or the constitutive cytosolic and active mutant (CaMKIIδB T287D/K328N/K329N).

FIGS. 3A-B—CaMKII-dependent phosphorylation of HDAC4 detected in a mammalian two-hybrid assay. (FIG. 3A) The N-terminal half of HDAC4 (amino acids 1-740) was fused to the GAL4 DNA binding domain and 14-3-3 was fused to the VP16 transcription activation domain. If GAL4-HDAC4 is not phosphorylated, it cannot recruit 14-3-3-VP16 and cannot activate the GAL4-dependent luciferase reporter. (FIG. 3B) As indicated, different GAL4-HDAC constructs were used in this assay in the absence and presence of CaMKIIδB-T287D. Cos cells were transfected with the indicated constructs. The increase in 14-3-3 binding is expressed as compared to control conditions without kinase. CaMKIIδB-T287D enhanced 14-3-3 binding to HDAC4 but only slightly to HDAC5. Substitution of Ser-467 or Ser-632 but not Ser-246 to alanine prevented the CaMKII induced increase in 14-3-3 binding.

FIGS. 4A-E—Mapping the CaMKII-responsive region of HDAC4. (FIG. 4A) Chimeric HDAC4/5 proteins (as indicated) were expressed in Cos cells in the presence of CaMKIIδB-T287D. Subcellular localization was verified by immunocytochemistry. Amino acids 529-657 were revealed to be required for nuclear export of HDAC4 in response to CaMKIIδB-T287D. (FIG. 4B) An HDAC5 mutant, in which the CaMKII consensus sites were mutated to the corresponding sites in HDAC4, was expressed in Cos cells alone or with CaMKI c.a. and CaMKIIδB-T287D. This mutant was responsive to CaMKI but again not to CaMKIIδB-T287D. (FIGS. 4C-4E) Co-immunoprecipitation assays with Cos cell lysates. (FIG. 4C) Cos cells were co-transfected with Flag-HDAC4 and either wild-type (WT) or constitutive activated (T287D) Myc-CaMKIIδB. Only the activated form of CaMKIIδB physically interacted with HDAC4. (FIG. 4D) Flag-HDAC4 deletion mutants were co-transfected with Myc-CaMKIIδB-T287D. (FIG. 4E) Amino acids 585-608 of HDAC4 were required for the physical interaction with CaMKIIδB-T287D and, therefore, define a CaMKII binding domain.

(FIG. 5A and FIG. 5B) Flag-HDAC4 mutants carrying point mutations in the CaMKII binding region were co-expressed with Myc-CaMKIIδB-T287D in Cos cells. Co-immunoprecipitation revealed that substitution of Arg-601 with either alanine or phenylalanine prevented a physical interaction with CaMKIIδB-T287D. (FIG. 5C and FIG. 5D) Cos cells were transfected with Myc-CaMKIIδB-T287D (red) or CaMKI c.a. and either Flag-HDAC4-wt, -R601A or -R601 (green) and localization was verified after one day using immunocytochemistry. HDAC4-R601A or F were still responsive to CaMKI, but not to CaMKIIδB-T287D and did not co-localize with the kinase. (FIG. 5C) Representative images. (FIG. 5D) Quantitative analysis. (FIG. 5E) Mammalian two-hybrid assay with GAL-HDAC4 mutants and VP-16-14-3-3. Substitution of Arg-601 with phenylalanine and leucine prevented and with alanine and lysine markedly attenuated 14-3-3 binding.

FIGS. 6A-F—Co-shuttling of HDAC4 and HDAC5. (FIG. 6A) In Cos cells, Flag-HDAC5 and Flag-MITR were expressed alone or with GFP-HDAC4 and subcellular localization was determined one day after transfection. CaMKIIδB-T287D induced nuclear export of HDAC5 and MITR in the presence of HDAC4, but not in its absence. Both localized to the same cytoplasmic dots. (FIG. 6B and FIG. 6C) Cos cells were transfectes with Myc-HDAC5 and Flag-HDAC4 and various deletion mutants of Flag-HDAC4. Co-immunoprecipitation revealed that HDAC5 binds to HDAC4 through its N-terminal extension (amino acids 1-200). (FIG. 6D) Flag-HDAC4 lacking the N-terminal amino acids 1-200 (Δ1-200) was expressed in Cos cells together with GFP-HDAC5. The N-terminal deletion abolished co-localization of HDAC4 with HDAC5 and prevented co-shuttling of HDAC5 to the cytosol in response to CaMKIIδB-T287D. (FIG. 6E) GFP-HDAC5 lacking the phosphorylation sites Ser-259 and -498 (S/A; green) was non-responsive to CaMKIIδB-T287D. When co-transfected together with Flag-HDAC4 (red), GFP-HDAC5 S/A was exported in response to CaMKIIδB-T287D. (FIG. 6F) GFP-HDAC5 and Flag-HDAC4 S/A were non-responsive to CaMKIIδB-T287D. When co-transfected together, both were exported in response to CaMKIIδB-T287D.

FIG. 10—Principle of the high content assay for screening CaMKII inhibitors. Cells are cotransfected with HDAC4-GFP and activated CaMKIIdB. Transfected cells are then treated with test compounds and CaMKII inhibitors can be identified by increased nuclear localization of HDAC4-GFP.

FIG. 11—Cellomics assay performance. Cell were palted on 384 well plates and transfected with HDAC4-GFP and activated CaMKII plasmid or control empty plasmid. Cells were fixed and imaged 48 hours later using the Cellomics array scanner using the nuclear translocation protocol. Nuclear to cytoplasmic differences in average GFP intensities were expressed as rwau values (top) or were normalized to the CaMKII treated cells (bottom). Assay statistics were calculated and shown. Avg, indicates average of values; stdev indicate standard deviation of values; S/B indicate signal to background values; S/N indicate signal to noise values; and z indicate z' values for these plates.

DESCRIPTION OF ILLUSTRATIVE EMBODIMENTS

I. The Present Invention

Figure 5A:
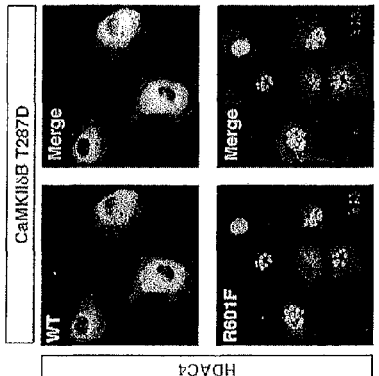
FIGS. 5A-E—Arg-601 of HDAC4 is required for full responsiveness to CaMKIIδB-T287D.

Cardiac hypertrophy is an adaptive response of the heart to various stress stimuli, including arterial hypertension, myocardial infarction, and mutations of sarcomeric proteins (Frey & Olson, 2003; Dorn et al., 2003). Stress-induced hypertrophy may initially normalize ventricular wall stress, but prolonged hypertrophic growth of the heart promotes ventricular dilation and sudden cardiac death (Frey & Olson, 2003; Dorn et al., 2003; Chien, K. R., 1999). At the cellular level, hypertrophy is associated with an increase in cardiomyocyte size, enhanced protein synthesis, heightened organization of sarcomere, and re-induction of a fetal cardiac gene program that eventually weakens cardiac performance (Frey & Olson, 2003; Dorn et al., 2003; Chien, K. R., 1999; Benjamin & Schneider, 2005). Thus, "transcriptional therapies" to suppress fetal gene activation have been proposed as a means of normalizing cardiac function in the settings of pathological hypertrophy and heart failure (McKinsey and Olson, 2005).

A complex web of signaling pathways has been implicated in the transmission of stress signals leading to cardiac hypertrophy and cardiac remodelling (Frey & Olson, 2003). Key questions in the field are whether there are nodal points of convergence among these hypertrophic pathways and how pathological signals are transmitted to downstream targets in the nucleus that reprogram cardiac gene expression. In this regard, the inventors and others have shown that changes in histone acetylation and deacetylation play a central role in the control of cardiac gene expression in response to stress signaling (Yanazume et al., 2003; Zhang et al., 2002; McKinsey & Olson, 2004; Gusterson et al., 2003). Histone acetylation by histone acetyltransferases (HATs) relaxes the structure of nucleosomes and favors gene activation (Roth et al., 2001). The HAT p300 has been shown to be essential for fetal gene activation in response to stress signaling (Yanazume et al., 2003; Zhang et al., 2002; McKinsey & Olson, 2004; Gusterson et al., 2003). Conversely, histone deacetylation promotes chromatin condensation and favors transcriptional repression.

Recently, the inventors have shown that class II histone deacetylases (HDACs) function as signal-dependent repressors of cardiac hypertrophy by regulating the activity of the myocyte enhancer factor-2 (MEF2) transcription factor, which regulates many fetal cardiac and stress-responsive genes (Edmondson et al., 1994; Passier et al., 2000; Naya et al., 1999). The class II HDACs (HDAC4, 5, 7 and 9) contain a C-terminal deacetylase domain and an N-terminal extension that mediates interactions with transcriptional repressors and activators (Benjamin & Schneider, 2005; Grozinger et al., 1999; Lu et al., 2000; Miska et al., 1999; Verdin et al., 2003). Interaction of MEF2 with the N-terminal extension of class II HDACs silences the expression of MEF2 target genes (Miska et al., 1999). Consistent with the notion that class II HDACs function as suppressors of pathological cardiac growth, mice lacking HDAC5 and HDAC9 are sensitized to hypertrophic stimuli (Zhang et al., 2002; Chang et al., 2004). Mice lacking HDAC4 and HDAC7 are not viable, which has precluded an analysis of the potential functions of these HDACs in cardiac hypertrophy in vivo.

The kinases that phosphorylate class II HDACs have become the focus of intense interest because they serve to connect extracellular stimuli with the genome by governing the nuclear localization and functions of class II HDACs. The inventors and others have shown that protein kinase D (PKD) transmits hypertrophic signals from G-protein coupled receptors to the regulatory phosphorylation sites in class II HDACs with consequent induction of cardiac hypertrophy (Vega et al., 2004; Parra et al., 2005; Dequiedt et al., 2005). In addition, CaM kinases I and IV (CaMKI and IV) have been shown in transfection assays to promote phosphorylation of class II HDACs, resulting in their dissociation from MEF2 and nuclear export in a 14-3-3 protein- and CRM1-dependent manner (McKinsey et al., 2000a; Davis et al., 2003; Kao et al., 2001; Kirsh et al., 2002; McKinsey et al., 2001; McKinsey et al., 2000b). However, these CaMK isoforms are unlikely to play a major role in hypertrophic signaling in cardiomyocytes since CaMKI activity is not increased during hypertrophy and CaMKIV is not expressed above background levels in the heart (Uemura et al., 1998; Colomer et al., 2003; Miyano et al., 1992).

Increasing evidence suggests that CaMKII is an important mediator in the transmission of calcium-dependent stress signals that control cardiomyocyte hypertrophy and activation of the fetal gene program (Colomer et al., 2003; Ramirez et al., 1997; Colomer and Means, 2000; Zhang et al., 2002; Zhang et al., 2005). For example, CaMKII activity is elevated in failing human hearts, and cardiac over-expression of CaMKII in transgenic mice induces pathological cardiac growth (Zhang et al., 2003; Hoch et al., 1999). Conversely, CaMKII inhibitors can prevent fetal gene induction in primary cardiomyocytes in vitro, while forced expression of an inhibitory CaMKII peptide in the hearts of transgenic mice can prevent hypertrophy and pathological cardiac remodeling following myocardial infarction or chronic adrenergic stimulation (Ramirez et al., 1997; Zhang et al., 2005; Kato et al., 2000). However, the downstream mediators that link CaMKII action with the cardiac genome have remained elusive.

Here, the inventors show that CaMKII selectively phosphorylates HDAC4 but not other class II HDACs. The selectivity of CaMKII signaling for HDAC4 is dependent on a unique CaMKII docking site within HDAC4 that is not present in other class II HDACs. The inventors also show that HDAC4 can confer CaMKII responsiveness to other class II HDACs through heterodimerization. Pharmacological blockade to CaMKII signaling or expression of a signal-resistant mutant of HDAC4 in cardiomyocytes blocks nucleocytoplasmic shuttling of HDAC4 in response to extracellular signaling and prevents hypertrophy. These findings reveal a mechanism for the transcriptional reprogramming of cardiomyocytes in response to CaMKII signaling and have implications for understanding the mechanism of action of CaMKII in a variety of cell types.

II. Histone Deacetylase

Nucleosomes, the primary scaffold of chromatin folding, are dynamic macromolecular structures, influencing chromatin solution conformations (Workman and Kingston, 1998). The nucleosome core is made up of histone proteins, H2A, HB, H3 and H4. Histone acetylation causes nucleosomes and nucleosomal arrangements to behave with altered biophysical properties. The balance between activities of histone acetyl transferases (HAT) and deacetylases (HDAC) determines the level of histone acetylation. Acetylated histones cause relaxation of chromatin and activation of gene transcription, whereas deacetylated chromatin generally is transcriptionally inactive. It was thus a novel finding and highly relevant to treatment of heart disease that HDAC's were shown to interact with MEF-2 and that HDAC's play a significant role in the control of the fetal gene program (see U.S. Pat. No. 6,706,686).

No less than 17 different HDACs have been cloned from vertebrate organisms. The first three human HDACs identified were HDAC 1, HDAC 2 and HDAC 3 (termed class I human HDACs), and HDAC 8 (Van den Wyngaert et al., 2000) was later added to the list of Class I HDACs. Later, class II human HDACs, HDAC 4, HDAC 5, HDAC 6, HDAC 7, HDAC 9, and HDAC 10 (Kao et al., 2000) were cloned and identified (Grozinger et al., 1999; Zhou et al. 2001; Tong et al., 2002). Additionally, HDAC 11 was identified (Gao et al., 2002), leading to the labeling of a third class of HDACs, Class III HDACs (Thiagalingam et al., 2003). All HDACs appear to share homology in the catalytic region. HDACs 4, 5, 7, 9 and 10 however, have a unique amino-terminal extension not found in class I HDACs. This amino-terminal region contains the MEF-2-binding domain. HDACs 4, 5, 7 and 9 have been shown to be involved in the regulation of cardiac gene expression and in particular embodiments, repressing MEF-2 transcriptional activity. The exact mechanism in which class II HDAC's repress MEF-2 activity is not completely understood. One possibility is that HDAC binding to MEF-2 inhibits MEF-2 transcriptional activity, either competitively or by destabilizing the native, transcriptionally active MEF-2 conformation. It also is possible that class II HDAC's require dimerization with MEF-2 to localize or position HDAC in a proximity to histones for deacetylation to proceed.

A variety of inhibitors for histone deacetylase have been identified. The proposed uses range widely, but primarily focus on cancer therapy. See Saunders et al. (1999); Jung et al. (1997); Jung et al. (1999); Vigushin et al. (1999); Kim et al. (1999); Kitazomo et al. (2001); Vigusin et al. (2001); Hoffmann et al. (2001); Kramer et al. (2001); Massa et al. (2001); Komatsu et al. (2001); Han et al. (2000). Such therapy is the subject of NIH sponsored clinical trials for solid and hematological tumors. HDAC's also increase transcription of transgenes, thus constituting a possible adjunct to gene therapy. (Yamano et al., 2000; Su et al., 2000). Perhaps the most widely known small molecule inhibitor of HDAC function is Trichostatin A, a hydroxamic acid. It has been shown to induce hyperacetylation and cause reversion of ras transformed cells to normal morphology (Taunton et al., 1996) and induces immunsuppression in a mouse model (Takahashi et al., 1996). It is commercially available from a variety of sources including BIOMOL Research Labs, Inc., Plymouth Meeting, Pa. A substantial listing of available HDAC inhibitors can be found below as well as in U.S. Pat. No. 6,706,686 and World Patent Application WO 04/112763 hereinafter incorporated by reference. U.S. Pat. No. 6,706,686 teaches the use of HDACi to treat and prevent cardiac hypertrophy and heart failure.

III. Deacetylase Inhibitors

A variety of inhibitors for histone deacetylase have been identified. The proposed uses range widely, but primarily focus on cancer therapy. Saunders et al. (1999); Jung et al. (1997); Jung et al. (1999); Vigushin et al. (1999); Kim et al. (1999); Kitazomo et al. (2001); Vigusin et al. (2001); Hoffmann et al. (2001); Kramer et al. (2001); Massa et al. (2001); Komatsu et al. (2001); Han et al. (2001). Such therapy is the subject of an NIH sponsored Phase I clinical trial for solid tumors and non-Hodgkin's lymphoma. HDAC's also increase transcription of transgenes, thus constituting a possible adjunct to gene therapy. Yamano et al. (2000); Su et al. (2000).

HDACs can be inhibited through a variety of different mechanisms—proteins, peptides, and nucleic acids (including antisense and RNAi molecules). Methods are widely known to those of skill in the art for the cloning, transfer and expression of genetic constructs, which include viral and non-viral vectors, and liposomes. Viral vectors include adenovirus, adeno-associated virus, retrovirus, vaccina virus and herpesvirus.

Also contemplated are small molecule inhibitors. Perhaps the most widely known small molecule inhibitor of HDAC function is Trichostatin A, a hydroxamic acid. It has been shown to induce hyperacetylation and cause reversion of ras transformed cells to normal morphology (Taunton et al., 1996) and induces immunsuppression in a mouse model (Takahashi et al., 1996). It is commercially available from BIOMOL Research Labs, Inc., Plymouth Meeting, Pa.

The following references, incorporated herein by reference, all describe HDAC inhibitors that may find use in the present invention: AU 9,013,101; AU 9,013,201; AU 9,013, 401; AU 6,794,700; EP 1,548,026; EP 1,233,958; EP 1,208, 086; EP 1,174,438; EP 1,173,562; EP 1,170,008; EP 1,123, 111; JP 2001/348340; U.S. 2002/103192; U.S. 2002/65282; U.S. 2002/61860; WO 05/75466; WO 05/71079; WO 05/66151; WO 05/65681; WO 05/58803; WO 05/51901; WO 05/40161; WO 05/40101; WO 05/30705; WO 05/30704; WO 05/19174; WO 05/14588; WO 05/00282; WO 04/113366; WO 04/113336; WO 04/92115; WO 04/87693; WO 04/82638; WO 04/13130; WO 02/51842; WO 02/50285; WO 02/46144; WO 02/46129; WO 02/30879; WO 02/26703; WO 02/26696; WO 01/70675; WO 01/42437; WO 01/38322; WO 01/18045; WO 01/14581; Furumai et al. (2002); Hinnebusch et al. (2002); Mai et al. (2002); Vigushin et al. (2002); Gottlicher et al. (2001); Jung (2001); Komatsu et al. (2001); Su et al. (2000).

IV. Calcium-Calmodulin Kinases

Calcium-calmodulin (CaM) dependent protein kinases are also members of the Serine Threonine Kinase (STK) family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, the cystic fibrosis conductance regulator protein, CFTR (Haribabu et al., 1995) and has been implicated in phosprylating proteins involved in cardiovascular disease (U.S. Pat. No. 6,201,165). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade."

Herein the inventors show that CaMKII transmits hypertrophic signals specifically to HDAC4, resulting in its nuclear export and derepression of the hypertrophic gene program. Inhibition of CaMKII prevents agonist-induced nucleocytoplasmic shuttling of HDAC4 in cardiomyocytes, and HDAC4 mutants lacking CaMKII phosphorylation sites are refractory to hypertrophic stimuli. Phosphorylation of HDAC4 by CaMKII requires a unique docking site that is absent in other class II HDACs. While HDAC5 and HDAC9 cannot respond directly to CaMKII, they dimerize with HDAC4, allowing them to be shuttled from the nucleus to the cytoplasm by HDAC4 in response to CaMKII signaling. These finding reveal a central role for the HDAC4/CaMKII partnership in the transmission of Ca2+-dependent hypertrophic stress-signals to the cardiac genome and expose previously unrecognized regulatory interactions between different class II HDACs. The ability of HDAC4 to selectively respond to CaMKII signaling has implications for the control of gene expression by calcium signaling in a variety of cell types.

V. Calpain

Calpain is present, in particular, in the cytoplasm of animal cells and is a cysteine protease which is activated by calcium. Several molecular species have been known in calpain. For analyzing the structure, their cDNA's have been cloned and, at present, the presence of μ- and m-calpain which are generally expressed in various tissues, as well as tissue-specific calpain such as, for example, p94 which is specifically expressed in a skeleton muscle is revealed (Seikagaku, 1993; Igaku, 1995).

Although details of physiological functions of calpain are not fully yet elucidated, calpain has been considered to have functions of a calcium receptor in cells and to be concerned in, for example, signal transduction, control of transcription, propagation and differentiation of cells, and the like. It is these implications that led the inventors to investigate the role of calpain in the CaMKII signaling pathway, and was a prelude to the discovery presented herein that calpain is capable of activating CaMKII through a proteolytic cleavage event.

VI. Hypertrophy And Hypertension

A. Hypertension

Hypertension, or high blood pressure, is a particularly significant problem in the adult population. This is because it is common, its consequences are far reaching and can be devastating and the symptoms do not show until late in its course, High blood pressure is one of the major risk factors for coronary heart disease and strokes. It can also lead to congestive heart failure, aortic dissection, and renal failure. Over half of patients with angina pectoris, sudden death, stroke, and atherothrombotic occlusion of the abdominal aorta or its branches have hypertension. Greater than 70% of people with dissecting aortic aneurysm, intracerebral hemorrhage, or rupture of the myocardial wall have high blood pressure. It is a major risk factor for atherosclerosis. Treatment of high blood pressure can prolong life. Screening programs reveal that 25% of the general population are hypertensive (Schoen, F. J., 1994). The prevalence of high blood pressure increases with age. However, in older age groups the disease is usually relatively mild compared to that in young adults where it is often more sever. Approximately 90 to 95% of hypertension is idiopathic and of the remaining 5 to 10%, most is secondary to renal disease. Hypertension can be classified as either primary or secondary, and can be found in the pulmonary compartment as well as other body compartments (i.e., renal). Both primary and secondary hypertension may be either benign or malignant.

In the majority of cases, hypertension remains at a modest level and fairly stable from years to decades. However, if the raised blood pressure is not controlled by anti-hypertensive agents, it frequently causes disability and death from heart failure, and substantially increases the risk of myocardial infarction and strokes. Approximately 5% of people have malignant hypertension where blood pressure rapidly increases and if left untreated, leads to death in one to two years. Recognizing the significance of the problem, it is an object of the present invention to provide a method of treating or prevent hypertension as well as its associated cardiovascular diseases.

1. Primary Hypertension

PH is a disease characterized by elevated arterial pressure with no apparent cause. PH may be further subclassified as primary pulmonary hypertension (PPH), which is also termed precapillary pulmonary hypertension or idiopathic pulmonary arterial hypertension, and is a less common form of PH where hypertension manifests as an elevation of pulmonary arterial pressure. The diagnosis of PPH is usually made after excluding other known causes of PH (Dresdale et al., 1951). The pathophysiology of PPH is poorly understood. It is believed that an insult of some kind (e.g., hormonal, mechanical, other) to the endothelium first occurs, resulting in a cascade of events characterized by vascular scarring, endothelial dysfunction, and intimal and medial (smooth muscle) proliferation. At least 10-15% of patients with PPH have a familial form, which has only recently been characterized. Some cases may be related to sporadic genetic defects (Oudiz et al., 2004).

Early in the disease, as the pulmonary artery pressure increases and the right ventricle must perform extra work, thrombotic pulmonary arteriopathy occurs. Thrombotic pulmonary arteriopathy is characterized by in situ thrombosis of small muscular arteries of the pulmonary vasculature. In later stages, as the pulmonary pressure continues to rise, plexogenic pulmonary arteriopathy develops. This is characterized by a remodeling of the pulmonary vasculature with intimal fibrosis and replacement of normal endothelial structure (Oudiz et al., 2004).

PPH has no cure, and left untreated, PPH leads inexorably leads to right-sided heart failure and death. The overall survival rate in one study was approximately 30% at 3 years. Prior to the 1990s, therapeutic options were limited. The recent emergence of prostacyclin analogues, endothelin receptor antagonists, and other novel drug therapies has greatly improved the outlook for patients with PPH and PPH-like diseases, but no one treatment is currently considered state of the art.

2. Secondary or PAH

Secondary pulmonary artery hypertension (SPAH) is defined as a pulmonary artery systolic pressure higher than 30 mm Hg or a pulmonary artery mean pressure higher than 20 mm Hg secondary to either a pulmonary or a cardiac disorder. If no etiology can be identified, the pulmonary arterial hypertension (PAH) is termed primary pulmonary hypertension. An increased volume of pulmonary blood flow, escalating resistance in the pulmonary vascular bed, or an elevation in pulmonary venous pressure can induce the rise in pulmonary arterial pressure (Oudiz et al., 2004).

Cardiac disorders, pulmonary disorders, or both in combination are the most common causes of secondary pulmonary hypertension. Cardiac diseases produce pulmonary hypertension via volume or pressure overload, although subsequent intimal proliferation of pulmonary resistance vessels adds an obstructive element. Perivascular parenchymal changes along with pulmonary vasoconstriction are the mechanism of pulmonary hypertension in respiratory diseases.

Therapy for secondary pulmonary hypertension is targeted at the underlying cause and its effects on the cardiovascular system. Novel therapeutic agents undergoing clinical trials have led to the possibility of specific therapies for these once untreatable disorders.

There are three predominant pathophysiologic mechanisms which may be involved in the pathogenesis of SPAH, (1) hypoxic vasoconstriction, (2) decreased area of the pulmonary vascular bed, and (3) volume/pressure overload (Oudiz et al., 2004). Chronic hypoxemia causes pulmonary vasoconstriction by a variety of actions on pulmonary artery endothelium and smooth muscle cells, including down-regulation of endothelial nitric oxide synthetase and reduced production of the voltage-gated potassium channel alpha subunit. Chronic hypoxemia leading to pulmonary hypertension can occur in patients with chronic obstructive pulmonary disease (COPD), high-altitude disorders, and hypoventilation disorders (e.g., obstructive sleep apnea).

COPD is the most common cause of SPAH. These patients have worse 5-year survival rates, more severe ventilation perfusion mismatch, and nocturnal or exercise-induced hypoxemia. Other disorders, such as obstructive sleep apnea, neuromuscular disorders, and disorders of the chest wall, may lead to hypoxic pulmonary vasoconstriction and eventually SPAH (Oudiz et al., 2004).

A variety of causes may decrease the cross-sectional area of the pulmonary vascular bed, primarily due to disease of the lung parenchyma. The pulmonary arterial pressure rises only when the loss of the pulmonary vessels exceeds 60% of the total pulmonary vasculature. Patients with collagen vascular diseases have a high incidence of SPAH, particularly patients with systemic scleroderma or CREST (calcinosis cutis, Raynaud phenomenon, esophageal motility disorder, sclerodactyly, and telangiectasia) syndrome. A mild-to-moderate elevation in mean pulmonary artery pressure occurs secondary to acute pulmonary embolism. The peak systolic pressures usually do not rise above 50 mm Hg, and they generally normalize following appropriate therapy. Chronic pulmonary emboli can result in progressive PAH. HIV infection and several drugs and toxins are also known to cause PAH (Oudiz et al., 2004).

Disorders of the left heart may cause SPAH, resulting from volume and pressure overload. Pulmonary blood volume overload is caused by left-to-right intracardiac shunts, such as in patients with atrial or ventricular septal defects. Left atrial hypertension causes a passive rise in pulmonary arterial systolic pressure in order to maintain a driving force across the vasculature. Over time, persistent pulmonary hypertension accompanied by vasculopathy occurs. This may occur secondary to left ventricular dysfunction, mitral valvular disease, constrictive pericarditis, aortic stenosis, and cardiomyopathy (Oudiz et al, 2004).

Pulmonary venous obstruction is a rare cause of pulmonary hypertension. This may occur secondary to mediastinal fibrosis, anomalous pulmonary venous drainage, or pulmonary venoocclusive disease. Increasing pulmonary arterial pressure is associated with a progressive decline in survival for patients with COPD or other interstitial lung diseases. The prognosis of patients with SPAH is variable and depends on the severity of hemodynamic derangement and the underlying primary disorder. Patients with severe pulmonary hypertension or right heart failure survive approximately 1 year. Patients with moderate elevations in pulmonary artery pressure (mean pressure<55 mm Hg) and preserved right heart function have a median survival of 3 years from diagnosis.

Although treatment of secondary pulmonary hypertension consists primarily of that necessary for the underlying disease, several medications and oxygen are used in different clinical settings. Currently, definite proof of effectiveness is lacking for several of these treatments (Oudiz et al., 2004). As such, there is a need for better medications for the treatment of PAH. PDE-III inhibitors have been suggested as a combination treatment in inhalants for treating pulmonary hypertension (Haraldsson et al., 2001; Schermuly et al., 2001), and could be beneficial for this disorder even as monotherapy.

B. Cardiac Hypertrophy and Cardiovascular Diseases

Heart failure is one of the leading causes of morbidity and mortality in the world. In the U.S. alone, estimates indicate that 3 million people are currently living with cardiomyopathy, and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familial dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunorubicin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including DCM, are significant public health problems.

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy.

With respect to myocardial infarction, typically an acute thrombocytic coronary occlusion occurs in a coronary artery as a result of atherosclerosis and causes myocardial cell death. Because cardiomyocytes are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

The causes and effects of cardiac hypertrophy have been extensively documented, but the underlying molecular mechanisms have not been fully elucidated. Understanding these mechanisms is a major concern in the prevention and treatment of cardiac disease and will be crucial as a therapeutic modality in designing new drugs that specifically target cardiac hypertrophy and cardiac heart failure. As pathologic cardiac hypertrophy typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses, so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities. The prognosis for patients with DCM is variable, and depends upon the degree of ventricular dysfunction, with the majority of deaths occurring within five years of diagnosis. The inventors describe herein a novel therapeutic composition and methods for treating pathologic cardiac hypertrophy and heart failure.

VII. Methods of Treating or Preventing Disease

A. Therapeutic Regimens

In one aspect of the present invention, methods for the treatment or prevention of cardiac hypertrophy, heart failure, dilated cardiomyopathy or hypertension are provided. For the purposes of the present application, treatment comprises reducing one or more of the symptoms of the above listed diseases, such as decreased exercise capacity, severe recurrent headache, decreased blood ejection volume, increased left ventricular end diastolic pressure, increased pulmonary capillary wedge pressure, decreased cardiac output, low cardiac index, increased pulmonary artery pressures, increased left ventricular end systolic and diastolic dimensions, increased left and right ventricular wall stress, or wall tension, decreased quality of life, disease-related morbidity and mortality, confusion and fatigue, chest pain, dyspnea, irregular heartbeat, blood in the urine. Prevention is defined as preventing the development of one or more of the symptoms associated with a disease in the presence of some stimulus (whether endogeous or exogenous) that could lead to the development of disease. Dosing regimens would vary depending on the clinical situation. However, both acute and long term maintenance therapies would be appropriate depending on the circumstances of the disease state or setting. It also may be desirable to treat a patient with the claimed therapeutics intermittently, such as within brief windows during disease progression; or prophylactically in the presence of a genetic or physiological background that would prime a patient for the development of renal or hypertensive disease.

Current treatments for hypertension, for example, entail a combination of lifestyle change and drug intervention therapies. Lifestyle changes, in and of themselves only partially effective at helping to control high blood pressure, may include weight loss, cessation of smoking, eating more fruits, vegetables, and low fat dairy products, less saturated and total fat, reducing the amount of salt in the diet to 2,400 milligrams (about 6 grams or 1 teaspoon) a day or less, getting regular aerobic exercise (such as brisk walking at least 30 minutes a day, several days a week), and limiting alcohol to two drinks a day for men, one drink a day for women. These measures not only help deal with the disease, they make the medicines used to treat hypertension more effective.

Current medicinal therapies for cardiac hypertrophy, heart failure, dilated cardiomyopathy or hypertension include a panoply of agents (for a complete listing of cardiovascular agents see U.S. Ser. No. 11/010,830 hereinafter incorporated by reference in its entirety) among which are angiotensin-converting enzyme (ACE) inhibitors, angiotensin receptor blockers (ARBs), diuretics, beta-blockers, calcium channel blockers, phosphodiesterase inhibitors, and endothelin receptor antagonists (ERAs such as ambrisentan, darusentan, bosentan, sitaxsentan, atrasentan). Each comes with various limitations, each of which (or all of which) may also be combined with agents that inhibit the CaMKII/HDAC4 interaction or the HDAC4/HDAC dimerization to more effectively treat the aforementioned diseases.

Preventive therapy would entail identifying patients at risk of developing cardiac hypertrophy, heart failure, dilated cardiomyopathy or hypertension and administering a compound that inhibits the CaMKII/HDAC4 interaction or the HDAC4/HDAC dimerization with or without additional therapy. Prevention could also be interpreted to mean prevention of worsening of the disease state, which would be accomplished by identifying a patient with cardiac hypertrophy, heart failure, dilated cardiomyopathy or hypertension and administering a compound that inhibits the CaMKII/HDAC4 interaction or the HDAC4/HDAC dimerization with or without additional therapy to prevent the further development of that disease.

B. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VIII. Screening

The present invention further comprises methods for identifying compounds that inhibit the CaMKII/HDAC4 interaction or HDAC4/HDAC dimerization that are useful in the prevention or reversal of cardiac hypertrophy, heart failure, dilated cardiomyopathy or hypertension. In unpublished data, it has been shown that calpain can cleave and activate CaMKII, so there are contemplated screens wherein a compound that inhibits the cleavage of CaMKII by calpain identifies that compound as a potential therapeutic agent. These assays may comprise random screening of large libraries of candidate substances; alternatively, the assays may be used to focus on particular classes of compounds selected with an eye towards structural attributes that are believed to make them more likely to function in the body, be bioavailable and have potency or efficacy.

To identify a compound of interest, one generally will determine the difference in binding of a protein (i.e., HDAC4) to another protein (i.e. CaMKII) in the presence and absence of the candidate substance; or one will determine the difference in cleavage of CaMKII by calpain; or finally, one may determine the difference in the ability of CaMKII to mediate the nuclear export of HDAC4, all of which will be done in the presence or absence of candidate compounds of interest. For example, a method generally comprises:

(a) providing a candidate compound;

(b) admixing the candidate compound with CaMKII (or calpain) and/or HDAC (in vivo or in vitro or in cyto);

(c) measuring a function of interest such as HDAC binding to CaMKII, CaMKII cleavage by calpain, or HDAC nuclear export as mediated by CaMKII; and (d) comparing the measured function in step (c) with the activity in the absence of the candidate modulator, wherein a difference between the measured functions indicates that the candidate compound is a compound capable of inhibiting the pro-hypertrophic cascade mediated by CaMKII signaling through the HDAC/MEF2 pathway. Assays may be conducted in isolated cells or in organisms. It will, of course, be understood that all the screening methods of the present invention are useful in themselves notwithstanding the fact that effective candidates may not be found. The invention provides methods for screening for such candidates, not solely methods of finding them.

As used herein the term "candidate compound" or an "agent" or a "therapeutic agent" refers to any molecule that may inhibit or potentially inhibit (1) the binding of either CaMKII or HDAC4 or class II HDACs, (2) the CaMKII-mediated nuclear export of HDAC4 from the nucleus of a cell, or (3) the activation of CaMKII by calpain cleavage in the appropriate assays needed to identify the candidate compound as a compound that could be used to treat or prevent any of the aforementioned diseases. The candidate compound may be a protein or fragment thereof, a small molecule, or even a nucleic acid. It may prove to be the case that the most useful pharmacological compounds will be compounds that are structurally-related to known HDACs or CaMKII. Using lead compounds to help develop improved compounds is known as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecular libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

2. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564. Large numbers of small peptide test compounds are synthesized on a solid substrate, such as plastic pins or some other surface. Such peptides could be rapidly screening for their ability to bind and inhibit HDACs.

i. In Vitro Biochemical Assay Designed to Identify Small Molecules that Disrupt the CaMKII/HDAC4 Interaction Leading to the Inhibition of Pro-hypertrophic CaMKII Signaling Through HDAC4

The principle of the assay is a homogenous time-resolved fluorescence resonance energy transfer (TR-FRET) proximity assay. In this approach, a complex between CaMKII and HDAC4 (or fragments of either) is established in solution and small molecules are incubated with this complex in order to identify compounds that are capable of disrupting the complex between CaMKII and HDAC4. TR-FRET involves the transfer of fluorescence energy between a fluorescence donor with a long fluorescence lifetime (e.g., chelates of the lanthanides Europium (Eu), Samarium (Sm) or Terbium (Tb)) and a fluorescence acceptor (e.g., allophycocyanin (APC)) that captures this energy and subsequently emits light at a longer wavelength than the excitation light or the emission wavelength of the free lanthanide chelate. Fluorescence energy transfer is a highly distance dependent phenomena and provides a useful tool to quantify the abundance of CaMKII/HDAC4 complexes in solution. In order to utilize this approach, each component of the complex must be labeled either directly or indirectly with the fluorescence donor or acceptor. Indirect labeling of the complex partners can be performed effectively by utilizing specific antibodies from two difference species (e.g., rabbit anti-HDAC4 and mouse anti-CaMKII) with corresponding secondary antibodies that are directly labeled with the fluorescence donor and acceptor (e.g., Eu-labeled goat-anti-rabbit IgG and APC labeled goat-anti-mouse IgG).

To conduct the assay, an appropriate molar ratio of CaMKII and HDAC4 (or fragments thereof) are incubated to establish a complex in solution. Specific antibodies to each component from different animal species, and the corresponding secondary antibodies that are labeled with Eu or APC are then incubated to establish a fluorescently labeled complex. A solution of a small molecule is then added to the fluorescently labeled complex and allowed to reach equilibrium. The amount of fluorescently labeled complex is then measured by exciting the sample with 340-nm light and measuring the fluorescence at 615 nm (emission of Eu in the absence of FRET to APC) and at 665 nm (APC fluorescence due to FRET from Eu) after a short time delay (typically 25 to 40 ms). The ratiometric fluorescence values (615 nm/665 nm) provide a measure of CaMKII/HDAC4 complex, and with the appropriate positive and negative controls can be used to quantify the changes in complex formation that are caused by the small molecule being investigated.

Alternative approaches to this assay that maintain the solution based homogenous proximity approach include the following: (1) the use of traditional FRET fluorescent molecule pairs (e.g., fluorescein and rhodamine) instead of using lanthanide chelates that have long fluorescence lifetimes. The principles of the assay are the same with the exception of the lack of a time delay before reading the fluorescence; (2) the use of a scintillation proximity assay (SPA), which involves the transfer of radioactive energy to a bead or crystal that contains a scintillant compound that releases light upon absorbing radioactive energy. In this approach, one of the members of the CaMKII/HDAC4 complex is indirectly labeled with a SPA bead or crystal and the other member is either directly or indirectly labeled with an appropriate radionuclide (e.g., $^3$H, $^{35}$S, $^{14}$C, $^{32}$P, etc.). Given the rapid decrease in the energy of a radioactive particle with distance, the corresponding SPA signal is also highly sensitive to the distance between the donor and acceptor molecules. This makes SPA a good alternative to the TR-FRET method. The AlphaScreen (PerkinElmer) is based on the same principles of using antibody intermediates to indirectly label the complex components. In this approach, the AlphaScreen donor and acceptor beads would replace the Eu and APC conjugated antibodies. The principle of this assay is that the donor bead is excited by laser light at 680 nm, which causes it to release singlet oxygen that has a limited diffusion distance in solution. The singlet oxygen reacts with thioxene derived compounds in the acceptor beads to produce chemiluminescent light at 520-620 nm. The distance dependence of singlet oxygen diffusion in solution also makes this assay very sensitive to the proximity of the two beads, which allows for the quantification of the amount of complex using the appropriate positive and negative controls; and the use of fluorescence polarization (FP). In this approach, either the HDAC4 or the CaMKII component of the complex would by necessity be a fluorescently labeled small peptide portion of the binding region (10-20 amino acids typically). Exciting the fluorescent peptide with plane polarized light will lead to a low level of polarized fluorescence if the peptide is not bound and a high level of polarization if the peptide is in a complex with the other component. This is determined by measuring the fluorescence of the sample in both the parallel and perpendicular planes to the plane of the polarized excitation light. A freely spinning/tumbling fluorescent peptide will produce fluorescence in both channels under a short measurement interval, whereas a slowly spinning/tumbling complex of fluorescent peptide with the other component will have a biased fluorescence in one channel during the same interval leading to greater fluorescence polarization.

Alternatives approaches that are discontinuous assays include the use of an enzyme linked immunosorbent assay (ELISA). This approach requires that one of the components is immobilized. The complex between CaMKII and HDAC4 is measured by evaluating the presence of the component that is not immobilized, after extensive washing, using an immunodetection method. This immunodetection method typically uses a primary antibody that recognizes the component that is not immobilized and a suitable secondary antibody that recognizes the primary antibody and is conjugated to an enzyme or molecule (e.g., horseradish peroxidase, alkaline phosphatase, fluorescent molecule) that allows for the quantification of the amount that component present after washing. The assay described above can utilize a lanthanide chelate conjugated secondary antibody (e.g., DELFIA technology from PerkinElmer), which makes the readout time resolved fluorescence.

ii. Inhibitors of Calpain-mediated Cleave of CaMKII

Calpain proteases have been shown to cleave CaMKII (data unpublished), resulting in constitutive activation of the kinase due to release of an auto-inhibitory domain. Described below are three complementary fluorescence-based in vitro biochemical assays to identify small molecules that inhibit calpain-mediated cleavage of CaMKII.

The first assay employs a reagent that quenches the fluorescent signal upon binding phosphoryl groups. A phosphoryl group and a fluorescent dye (Pierce) will be coupled to opposing ends of a synthetic peptide substrate for calpain that is based on sequences from human CaMKII. The peptide could match peptides from CaMKII $\alpha$, $\beta$, $\delta$ or $\gamma$, given the conservation of the calpain cleavage site among these four family members. Many isoforms of calpain exist. The assay will likely employ recombinant forms of either m-calpain or $\mu$-calpain, given prior studies implicating these isoforms in the control of pathological processes in the heart. The assay will be optimized for linearity based on substrate/enzyme concentrations and time.

To conduct the assay, an appropriate molar concentration of tagged CaMKII peptide will be mixed in wells of 384-well dishes with enzyme reaction buffer contain calcium, which is required for calpain action. A solution of small molecule will then added to reaction mixtures and allowed to reach equilibrium. Finally, calpain will be added to wells and reactions allowed to proceed for an appropriate length of time prior to addition of fluorescence quenching reagent. Effects of small molecules on calpain-directed cleavage of the peptide will be determined by exciting the samples with 560-nm light and measuring the fluorescence at 590-nm (emission of the fluorescent dye) using a fluorescence plate reader. Control wells will contain various combinations of small molecule vehicle, calpain and peptide to ensure that fluorescence signal is representative of calpain-mediated cleavage of the CaMKII peptide. In addition, some reactions will be performed in the presence of a calcium-chelator such as BAPTA, which completely blocks calpain activity, or small molecule inhibitors of calpain, such as PD150606 (Calbiochem), which will serve as reference compounds for assay performance. A small molecule inhibitor of calpain-directed cleavage of CaMKII peptide will reduce fluorescence signaling, since the phosphoryl-group (bound by quenching reagent) will remain in close proximity to the fluorophore.

An alternative screening approach for identification of small molecule inhibitors of calpain-directed cleavage of CaMKII involves the use of fluorescence resonance energy transfer (FRET). FRET relies on the transfer of fluorescence energy between a fluorescence donor with a long fluorescence lifetime (e.g., chelates of lanthanides Europium, Samarium or Terbium) and a fluorescence acceptor (e.g., allophycocyanin) that captures the energy and emits light of a longer wavelength than the excitation light. A fluorescence donor and acceptor will be coupled to opposing ends of a synthetic peptide substrate for calpain that is based on sequences from human CaMKII (see above). The assay conditions will be as described above. Effects of small molecules on FRET signal will be determined by exciting samples with 340 nm light and measuring fluorescence at 615 nm (emission of Eu in the absence of FRET to APC) and at 665 nm (APC fluorescence due to FRET from Eu). Ratiometric fluorescence values (615 nm/665 $\mu$m) will provide a measure of the extent of peptide cleavage by calpain. Calpain-directed cleavage of the CaMKII peptide will reduce fluorescence signal, and a small molecule inhibitor of calpain will maintain fluorescence signal.

A third approach relies on the use of CaMKII peptide coupled to Amino-4-methylcoumarin (AMC). Upon its release from the peptide following cleavage by calpain, AMC can be measured fluorometrically using an excitation wavelength of ~360-380 nm and an emission wavelength of ~440-460 nm. Assays will be run in 384-well dishes and fluorescence measured using a plate reader, as described above.

3. In Cyto Assays

The present invention also contemplates the screening of compounds for their ability to modulate HDACs in cells. Various cell lines can be utilized for such screening assays, including cells specifically engineered for this purpose.

Figure 8:
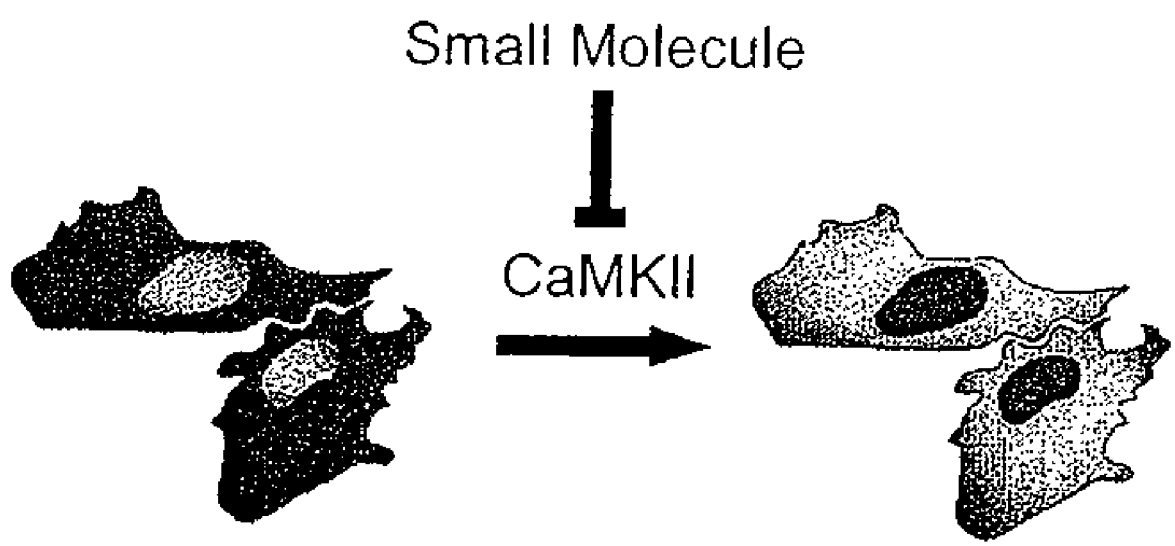
FIG. 8—Picture of HDAC nuclear localization as imaged by Cellomics.

High content assays are cell based assays that utilize image capture and analysis software to measure biological responses. One of the applications of High Content Assay technology is to quantify localization of specific molecules in various sub-cellular organelles or locations. High content screening utilizes fluoresce microscopy and specifically tagged molecules to track their location in the cell. This method can be applied in a screen for CaMKII inhibitors. This is because CamKII was shown to cause export of HDAC4 from the Nucleus (FIG. 8).

Figure 9:
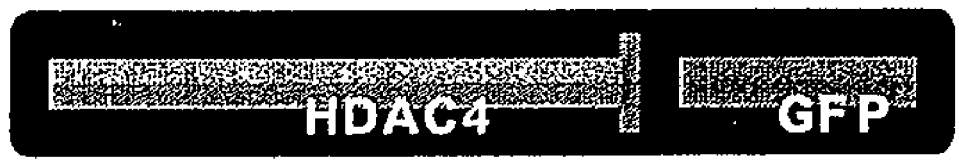
FIG. 9—HDAC-GFP fusion protein.

Briefly, for the assay, mammalian cells (COS, or 293T or 10T1/2 or H9C2 or NRVM) are transfected or infected with two genetic constructs. One encoding a tagged activated HDAC4, and the other an activated CamKII. Examples of tagged HDAC4 include carboxyterminal fusion to GFP (FIG. 9), or carboxyterminal fusion of short epitope peptides such as myc, HA, flag, or 6histidine. Genetically activated CamKII includes a recombinant gene for CamKIIdb that contains the mutation in position 287 from T to D (T287D). This amino acid change mimics an activating phosphorylation event on T287 that occurs in the native enzyme upon activation by Ca++ and calmodulin.

Following transfection or infection, cells are plated in 384-well plates and incubated overnight at 37° C., 5% $CO_2$. The next day the media from these cells is replaced with fresh media, dosed with test compounds, and continued to incubate for 24-48 hrs. The cells are then fixed (formalin or glutaraldehyde or ethanol or methanol) and nuclei are counterstained with Hoechst or DAPI and if small peptide tagged HDAC5 is used the cells are immunostained using primary antibody specific for the tag used and a fluorescently labeled secondary antibody (for example fluorescein labeled). No antibody staining is necessary if GFP is used as tag.

Stained plates are imaged in the cellomics station using the Nuclear Translocation algorithm. This algorithm is used to quantify the amount of label present in the nuclear versus the cytoplasmic compartment. This is accomplished as follows. There are two images taken for each field. One at the wavelength emitted by the nuclear stain (DAPI or Hoechst), and the other at the wavelength emitted by the label of the HDAC4. The algorithm is utilizing the DAPI or Hoeches image to locate the cells by virtue of their fluorescent nuclei. This image is converted into a binary mask where the nuclei have a single bright value and the background the second dark value of the binary scale. This mask is used to define the fringe of the nucleus of each cell. The algorithm then generates an area on the CCD chip corresponding to the nuclear space based on intensity value of the binary mask. Then the algorithm measures a defined and pre-specified number of pixels outward that generates a ring area surrounding the nuclear are. This represents the perinuclear area which is a section of the cytoplasmic area. The algorithm then utilizes an image from the HDAC specific wavelength and obtains average intensity values for the nuclear and perinuclear are. The difference of the two values is a measure of the relative brightness of the nucleus versus the cytoplasm. Therefore a low value for this delta indicates cytoplasmic localizations whereas a high delta indicates a nuclear localization.

Cells treated with compounds that have no effect in CamKII activity will have relatively low deltas whereas cells that were treated with CamKII inhibitors will have high delta values.

Depending of the tags used this assay can have different permutations. More information on these assays can be found in U.S. Patent Application 20050227268 and WO 00/19966, hereinafter incorporated by reference.

4. In Vivo Assays

In vivo assays involve the use of various animal models of heart disease, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to. Also, measuring toxicity and dose response can be performed in animals in a more meaningful fashion than in in vitro or in cyto assays.

IX. Definitions

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the terms "antagonist" and "inhibitor" refer to molecules or compounds which inhibit the action of a cellular factor that may be involved in cardiac hypertrophy. Antagonists may or may not be homologous to these natural compounds in respect to conformation, charge or other characteristics. Thus, antagonists may be recognized by the same or different receptors that are recognized by an agonist. Antagonists may have allosteric effects which prevent the action of an agonist. Alternatively, antagonists may prevent the function of the agonist. In contrast to the agonists, antagonistic compounds do not result in pathologic and/or biochemical changes within the cell such that the cell reacts to the presence of the antagonist in the same manner as if the cellular factor was present. Antagonists and inhibitors may include proteins, nucleic acids, carbohydrates, or any other molecules which bind or interact with a receptor, molecule, and/or pathway of interest.

As used herein, the term "modulate" refers to a change or an alteration in the biological activity. Modulation may be an increase or a decrease in protein activity, a change in binding characteristics, or any other change in the biological, functional, or immunological properties associated with the activity of a protein or other structure of interest. The term "modulator" refers to any molecule or compound which is capable of changing or altering biological activity as described above.

The term "$\beta$-adrenergic receptor antagonist" refers to a chemical compound or entity that is capable of blocking, either partially or completely, the beta ($\beta$) type of adrenoreceptors (i.e., receptors of the adrenergic system that respond to catecholamines, especially norepinephrine). Some $\beta$-adrenergic receptor antagonists exhibit a degree of specificity for one receptor sybtype (generally $\beta_1$); such antagonists are termed "$\beta_1$-specific adrenergic receptor antagonists" and "$\beta_2$-specific adrenergic receptor antagonists." The term $\beta$-adrenergic receptor antagonist" refers to chemical compounds that are selective and non-selective antagonists. Examples of $\beta$-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known $\beta$-adrenergic receptor antagonists is encompassed by the methods of the present invention. Indeed any compound, which functionally behaves as a $\beta$-adrenergic receptor antagonist is encompassed by the methods of the present invention.

X. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Example 1

1. Materials and Methods

Chemical reagents and plasmids. Phenylephrine (PE) and isoprenaline (Iso) were purchased from Sigma Chemical (St. Louis, Mo.). KN93, KN62, autoctamide-2 related inhibitory peptide II (AIPII-2), staurosporine, bisindolylmaleimide I (Bis), Gö6976 and cyclosporin A (CSA) were obtained from Calbiochem (La Jolla, Calif.), leptomycin B was purchased from LC Laboratories (Woburn, Mass.).

Epitope-tagged derivates of the CaMKII$\delta$ splicing variants A, B and C, CaMKII$\gamma$A, CaMKII$\alpha$A and CaMKII$\beta$'e, containing amino-terminal Myc tags were generated using the pcDNA3 expression vector (Invitrogen). HDAC7 was fused to an amino-terminal FLAG tag (pcDNA3), and HDAC4 to a carboxy-terminal GFP tag (EGFPN1; Clontech). Epitope-tagged derivatives of constitutively active CaMKI (created by a deletion of the autoinhibitory domain at the C-terminus), HDAC4, HDAC5 and MITR, containing HA, FLAG, Myc or GFP tags were described previously 6, 21, 25, 26, 54. Point mutations were introduced with the Quikchange kit (Stratagene). Deletion mutants of HDAC4 were generated by PCR with PFU Turbo polymerase (Stratagene).

Cardiomyocyte culture and adenoviral infection. NRVMs were isolated from 1-2 day Sprague Dawley rats. For adenovirus production, cDNAs encoding FLAG-tagged HDAC4 wild-type or a mutant containing alanines in place of serines 246, 467 and 632 (S/A) were subcloned into the pACCMV vector and co-transfected with pJM17 into 293 cells. Primary lysates were used to re-infect 293 cells and viral plaques were obtained using the agar overlay method. The production of adenoviral GFP-HDAC5 was described previously 18. NRVMs were infected 24 h after plating, starved for 4 h, and stimulated with PE or Iso for the indicated time period. In experiments with kinase inhibitors, NRVMs were pretreated with the inhibitor 30 min prior stimulation. For assessing cardiomyocyte hypertrophy, NRVMs were starved for 24 h and stimulated with PE for another 24 hrs. Subcellular localization of Flag-HDAC4 and cardiomyocyte hypertrophy, as assessed by sarcomeric organization, was determined by indirect immunofluorescence.

Cell culture and transfection assays. COS cells were maintained in DMEM with fetal bovine serum (10%), L-glutamine (2 mM), and penicillin-streptomycin. Transfection of COS cells was performed with Fugene 6 (Roche Molecular Biochemicals) according to manufacturer's instructions.

Indirect Immunofluorescence. COS cells were grown on glass coverslips, fixed in paraformaldehyde (4%), permeabilized in 0.1% Triton-X-100 and blocked in PBS containing goat serum (5%). Primary antibodies against FLAG (monoclonal or rabbit; Sigma), Myc (polyclonal, A-14; Santa Cruz), or HA (polyclonal, Y-11; Santa Cruz) were used at a dilution of 1:200. Secondary antibodies conjugated to either fluoresceine or Texas Red (Vector Laboratories) were also used at a dilution of 1:200. Staining of NRVMs for sarcomeres was performed with an antibody directed against sarcomeric $\alpha$-actinin (Sigma). All images were captured at a magnification of ×40.

Endogenous MEF2 activity in NRVMs. One day after plating, a MEF2 dependent luciferase reporter $(3xMEF2-Luc)_{56}$, carrying three MEF2-DNA binding sites, was transfected into NRVMs using Lipofectamine plus (Invitrogen; Carlsbad, Calif.). To control for transfection efficiency NRVMs were cotransfected with a $\beta$-galactosidase reporter plasmid (pCMV-lacZ). Twenty-four hours after transfection, NRVMs were starved for 24 h, pretreated with kinase inhibitors or cyclosporine for 30 min and stimulated with ionomycin for 24 h. Luciferase and $\beta$-galactosidase levels were quantified employing the Luciferase Assay Kit (Promega) and the Fluo-Reporter Kit (Molecular probes), respectively.

Mammalian two-hybrid analysis. A mammalian expression vector encoding the GAL4 DNA binding domain fused to the amino-terminus of human HDAC4 (amino acids 2-740) was generated in the pM expression vector (Clontech). GAL4-HDAC4 fusions harboring alanine in place of either Ser-246, -467 or -632 and alanine, phenylalanine, lysine or leucine in place of Arg-601 were constructed in an analogous manner. A construct encoding the herpes virus VP16 transcriptional activation domain fused to the amino terminus of 14-3-3 sigma was generated employing pVP16 (Clontech). COS cells were transiently transfected with vectors for GAL4-HDAC4, VP16-14-3-3 and a luciferase reporter gene under the control of five copies of a GAL4 DNA binding site (5xUAS-luciferase) in the absence or presence of a construct encoding constitutively active CaMKIIδB. Transfection efficiency was controlled by cotransfection of pCMV-lacZ. Twenty-four hours post-transfection, cells were harvested and luciferase and β-galactosidase levels were determined as described above.

Coimmunoprecipitation and immunoblotting. COS cells were harvested one day posttransfection in Tris (50 mM, pH 7.4), NaCl (800 mM), EDTA (1 mM), and Triton X-100 (1%) supplemented with protease inhibitors (Complete; Roche) and phenylmethylsulfonyl fluoride (PMSF; 1 mM). Cells were further disrupted by passage through a 25-gauge needle and cell debris removed by centrifugation. FLAG-tagged proteins were immunoprecipitated with M2-agarose conjugate (Sigma) and thoroughly washed with lysis buffer. Bound proteins were resolved by SDS-PAGE, transferred to PVDF membranes and immunoblotted as indicated with either anti-Myc antibody (polyclonal, A-14; Santa-Cruz), or a monoclonal ant-FLAG antibody (M2; Sigma). Proteins were visualized with a chemiluminescence system (Santa Cruz).

2. Results

CaMKII induces cardiomyocyte hypertrophy via HDAC4. To begin to investigate the potential involvement of HDAC4 in hypertrophic signaling, the inventors infected neonatal rat ventricular myocytes (NRVMs) with an adenovirus encoding FLAG-HDAC4 and examined the subcellular distribution of HDAC4 in response to hypertrophic agonists. Stimulation with the adrenergic agonists phenylephrine (PE), which acts through alpha-adrenergic receptors, or isoprenaline (Iso), which acts through beta-adrenergic receptors, evoked a hypertrophic growth response (not shown) and caused a time-dependent nuclear export of HDAC4 (FIG. 1A and FIG. 1B).

To characterize the kinases that mediate HDAC4 nuclear export in response to these agonists, the inventors pretreated cardiomyocytes with a variety of kinase inhibitors (FIG. 1A and FIG. 1C). PE-induced export of HDAC4 was markedly reduced by the general serine/threonine kinase inhibitor staurosporine, as well as by the CaMKII inhibitors KN93, KN62 and AIPII. In contrast, bisindolylmaleimide I (BisI), Gö6976, and H89, which preferentially inhibit PKC, PKD and PKA, respectively, did not affect HDAC4 localization. Consistent with our previous findings that the PKC-PKD axis regulates HDAC5 export18, PE-induced export of over-GFP-HDAC5 was not affected by KN93 (FIG. 1A).

HDAC4 contains three signal-responsive serines (Ser-246, -467, and -632) that serve as docking sites for 14-3-3 proteins which mediate nuclear export of HDACs26, 31, 37. Whereas wild-type HDAC4 did not prevent sarcomeric organization of NRVMs, because it was exported from the nucleus, a signal-resistant HDAC4 mutant in which these serines were replaced with alanines (S246/467/632A) completely blocked the hypertrophic response to PE, suggesting that CaMKII-induced nucleocytoplasmic shuttling of HDAC4 is an essential step in the induction of myocyte hypertrophy (FIG. 1D).

To check whether CaMKII activation increases eventually MEF2 activity in cardiomyocytes, the inventors transfected NRVMs with a MEF2-dependent luciferase reporter carrying three MEF2 DNA binding sites (3xMEF2-Luc) and stimulated endogenous CaMKII with the calcium ionophore ionomycin (FIG. 1E). Ionomycin doubled the MEF2 activity, and this increase was blocked by the CaMKII inhibitors KN93 and KN62 but not by the calcineurin inhibitor cyclosporine A (CSA), suggesting that the increased MEF2 activity was entirely mediated by CaMKII and not by calcineurin A, which is also an ionomycin-responsive regulator of hypertrophy. The observation, that the PKD inhibitor Gö6976 did not affect the ionomycin-mediated increase in MEF2 activity suggests that the PKC-PKD axis is not directly involved in calcium-dependent signalling.

CaMKII specifically induces nucleocytoplasmic shuttling of HDAC4. To directly test the role of CaMKII in nucleocytoplasmic shuttling of class II HDACs, the inventors transfected COS cells with expression plasmids encoding HDAC4, 5, 7 and MITR (a splice variant of HDAC9) and constitutively active forms of CaMKII carrying point mutations (T287D) that mimic autoactivation. HDAC4 was completely exported from the nucleus by all activated CaMKII isoforms and became localized in punctuate dots in the cytoplasm. In contrast, the other class II HDACs did not change their predominant nuclear localization in response to activated CaMKIIδ, γ, β, or α (FIG. 2A and FIG. 2B and data not shown). A constitutively active form of CaMKI induced nucleocytoplasmic shuttling of HDAC4, 5 and 7 and changed the nuclear distribution of MITR, which lacks a nuclear export sequence (NES), from punctuate to homogeneous. These results revealed that HDAC4 was uniquely responsive to CaMKII.

HDAC4 co-localizes with activated CaMKII. To begin to explore the mechanistic basis for the selective responsiveness of HDAC4 to CaMKII signaling, the inventors examined whether CaMKII and HDAC4 might be co-localized in cells. The CaMKIIδ splicing variant B contains a nuclear localization signal (NLS) and thus likely targets nuclear proteins38. Unexpectedly, activated CaMKIIδB (T287D) localized predominantly to the cytosol, in contrast to the wild-type (inactive) form, which was mainly localized to the nucleus (FIG. 2C). Phosphorylation of Ser-332 by CaMKI and IV within the NLS (328KRKKSSSS335) of CaMKIIδb has been shown to induce nucleocytoplasmic shuttling of CaMKIIδb38,39. To test whether activated CaMKII stimulates another kinase or autophosphorylates itself at Ser-332, the inventors introduced an additional point mutation (K43M) in CaMKIIδb-T287D, which eliminated its catalytic activity. This CaMKIIδb double mutant also localized to the cytosol (data not shown). Therefore, the inventors postulate that mimicking autophosphorylation of CaMKIIδb by a T287D mutation changes its conformation, which allows other kinases (presumably CaMKI or IV) to phosphorylate Ser-332. Despite its predominant cytosolic localization, CaMKIIδb-T287D potently localized HDAC4 to the cytosol. The CaMKIIδ splice variants A and C, CaMKIIδA and CaMKIIδ'e, which do not contain a NLS exerted the same effect on HDAC4 localization as CaMKIIδb (data not shown). Likewise, a CaMKIIδb mutant, in which the NLS was destroyed38 (T287D/K328N/K329N) localized exclusively to the cytosol but also induced nucleocytoplasmic shuttling of HDAC4 (FIG. 2E).

The fact that CaMKIIδb-T287D is predominantly cytosolic, while HDAC5 is exclusively nuclear in unstimulated cells raised still the possibility that the insensitivity of HDAC5 to CaMKII might reflect its sequestration in a different subcellular compartment than CaMKII. The inventors therefore generated a double mutant (CaMKIIδb-T287D/S332A), resulting in a constitutively active and nuclear form of the protein (FIG. 2C). As shown in FIG. 2D, this mutant form of CaMKII, like CaMKII-T287D, induced nucleocytoplasmic shuttling of HDAC4 but not HDAC5. Remarkably, although CaMKIIδbT287D/S332A cannot be phosphorylated within its NLS and is clearly localized to the nucleus when expressed in the absence of HDAC4, it co-localized with HDAC4 to the cytosol, suggesting a possible physical interaction between HDAC4 and CaMKII that results in co-shuttling of the two proteins to the cytosol.

HDAC4 was located in the cytosol in approximately 20-30% of cells under basal conditions. To determine whether CaMKII induces nuclear export or blocks nuclear import of HDAC4, the inventors examined the effect of leptomycin B, an inhibitor of CRM1-dependent nuclear export, on the intracellular redistribution of HDAC4 in response to different active CaMKIIδb mutants (FIG. 2E). After treatment with leptomycin B, HDAC4 completely accumulated in the nucleus in the absence (not shown) and presence of the constitutive nuclear (and active) form of CaMKIIδb (T287D/S332A), suggesting that this mutant induced nuclear export of HDAC4. In contrast, in the presence of the constitutive cytosolic (and active) CaMKIIδb mutant (T287D/K328N/K329N) as well as the CaMKIIδb T287D mutant, leptomycin B induced no accumulation of HDAC4, indicating that these mutants block nuclear import. Therefore, the inventors postulate that, dependent on its subcellular localization, CaMKII is able to do both to block nuclear import or to induce nuclear export of HDAC4.

Analysis of HDAC4 phosphorylation using a two-hybrid assay. Phosphorylation of HDAC4 correlates with 14-3-3-binding. Therefore, to examine the effect of CaMKII on the phosphorylation state of HDAC4, the inventors performed a mammalian two-hybrid assay (FIG. 3A) using the N-terminal half of HDAC4 (amino acids 1-740) fused to the GAL4 DNA binding domain and 14-3-3 was fused to the VP16 transcription activation domain. In the absence of CaMKII, GAL4-HDAC4 is not phosphorylated and cannot recruit 14-3-3-VP16. Hence, a GAL4-dependent luciferase reporter cannot be activated. However, in the presence of CaMKII, HDAC4 is phosphorylated, which creates docking sites for 14-3-3-VP16 and consequent activation of the GAL4-dependent reporter. Thus, the degree of 14-3-3 binding to HDAC4 and luciferase expression reflects the phosphorylation state of HDAC4 at 14-3-3 docking sites.

CaMKIIδb-T287D stimulated the expression of the GAL4-dependent luciferase reporter in the presence of GAL4-HDAC4 and 14-3-3-VP16 (FIG. 3B). In contrast, CaMKIIδb-T287D failed to activate the reporter in the presence of GAL4-HDAC5 and 14-3-3-VP16, confirming the selective responsiveness of HDAC4 to CaMKII.

To identify the phosphorylation sites of HDAC4 targeted by CaMKIIδb-T287D, the inventors replaced each of the three signal-responsive serines (Ser-246, -467 and -632) with alanines. Disruption of Ser-246 did not affect the interaction of 14-3-3 with HDAC4 in response to CaMKIIδbB-T287D. In contrast, disruption of Ser-467 or Ser-632 dramatically reduced 14-3-3 binding. Disruption of Ser-246 and Ser-467, Ser-467 and Ser-632 or all three serines completely abolished 14-3-3 binding (not shown). In simultaneous control experiments with constitutively active CaMKI (data not shown), disruption of Ser-246 also did not affect the interaction of HDAC4 with 14-3-3. Mutation of Ser-467 resulted in about a 90% reduction in 14-3-3 binding, while mutation of Ser-632 caused about a 50% reduction in the presence of CaMKI compared to wild-type HDAC4. Therefore, in contrast to HDAC5, in which Ser-259 and Ser-498 (which correspond to Ser-246 and Ser-467 of HDAC4) are the key phosphorylation sites for PKD signaling, Ser-467 and Ser-632 in HDAC4 are the most critical sites for 14-3-3 binding in response to CaMKII signaling. Moreover, while CaMKI preferentially acts on Ser-467, CaMKII appears to phosphorylate Ser-467 and -632 of HDAC4 to a similar degree.

Mapping a CaMKII responsive region of HDAC4. To further examine the molecular basis for the selective responsiveness of HDAC4 to CaMKII, the inventors generated mutant constructs encoding chimeric HDAC4/HDAC5 proteins. As shown in FIG. 4A, only those chimeric proteins containing residues 529-657 of HDAC4 were responsive to CaMKIIδb-T287D. Because this region contains Ser-632, the inventors asked whether this phosphorylation site determines the selective responsiveness of HDAC4 to CaMKIIδb-T287D. The amino acid sequence surrounding Ser-632 of HDAC4 differs at four positions from the corresponding region in HDAC5, which surrounds Ser-661. The inventors mutated these three residues in addition to two differing amino acids in the consensus sequence around Ser-498 of HDAC5 to those of HDAC4 (HDAC5 S494G, S499A, G657S, T659A, A665S). Despite these changes, this HDAC5 mutant was still non-responsive to CaMKII (FIG. 4B). These results suggested that differences in the CaMKII phosphorylation sites of HDAC5 were insufficient to account for its insensitivity to CaMKII.

Activated CaMKII interacts with a unique domain of HDAC4. Based on the observation that activated CaMKII (T287D) co-localized with HDAC4, the inventors performed immunoprecipitation experiments to determine if the proteins interacted. As shown in FIG. 4C, the inventors found that activated CaMKII (T287D) but not inactive wild type CaMKII strongly bound to HDAC4. These findings suggest that autophosphorylation induces a conformational change in CaMKII, which allows it to bind to HDAC4. In contrast, CaMKIIδb-T287D did not interact with HDAC5, 7 or MITR (data not shown), suggesting that HDAC4 possesses a unique domain that mediates binding to the kinase.

Coimmunoprecipitation experiments using deletion mutants of HDAC4 resolved the CaMKII binding domain to amino acids 585-608 of HDAC4 (FIG. 4D and FIG. 4E). Although HDAC4 shares extensive amino acid homology with other class II HDACs throughout its length, this CaMKII binding region is not homologous to other class II HDACs (FIG. 5A).

Figure 5C:
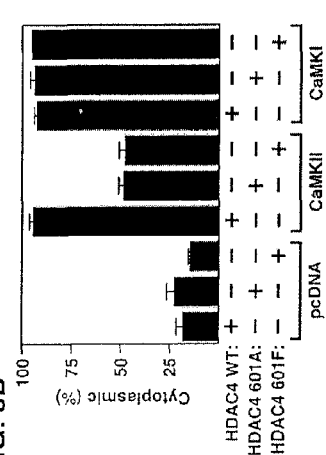
Figure 5D:
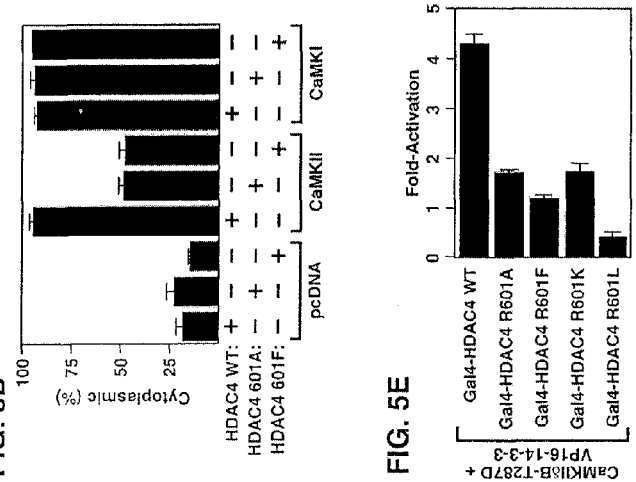
Figure 5B:
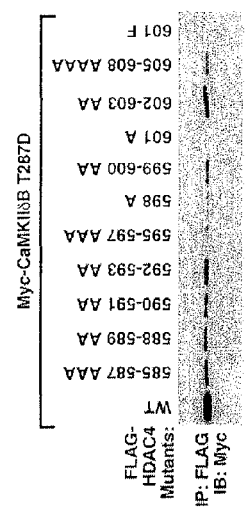

To pinpoint the residue(s) required for interaction of HDAC4 with CaMKII, the inventors systematically mutated all charged residues in the minimal CaMKII binding domain to alanines and tested the mutants for their ability to bind CaMKII by co-immunoprecipitation. As shown in FIG. 5A and FIG. 5B, substitution of Arg-601 to alanine or phenylalanine markedly disrupted the physical interaction between HDAC4 and CaMKII.

To test whether Arg-601 of HDAC4 was required for CaMKII responsiveness, the inventors examined the subcellular localization of two HDAC4 mutants (R601A and R601F) in the presence of CaMKIIδB-T287D. In contrast to wild-type HDAC4, these mutants failed to be entirely exported from the nucleus by CaMKIIδB-T287D (FIG. 5C and FIG. 5D). Moreover, these HDAC4 mutants did not co-localize with CaMKIIδB-T287D. In contrast, HDAC4 R601A and R601F mutants were still responsive to CaMKI (FIG. 5D), indicating that Arg-601 is specifically required for CaMKII sensitivity.

Figure 5E:
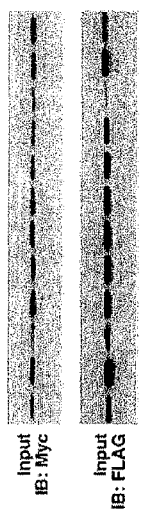
Figure 7:
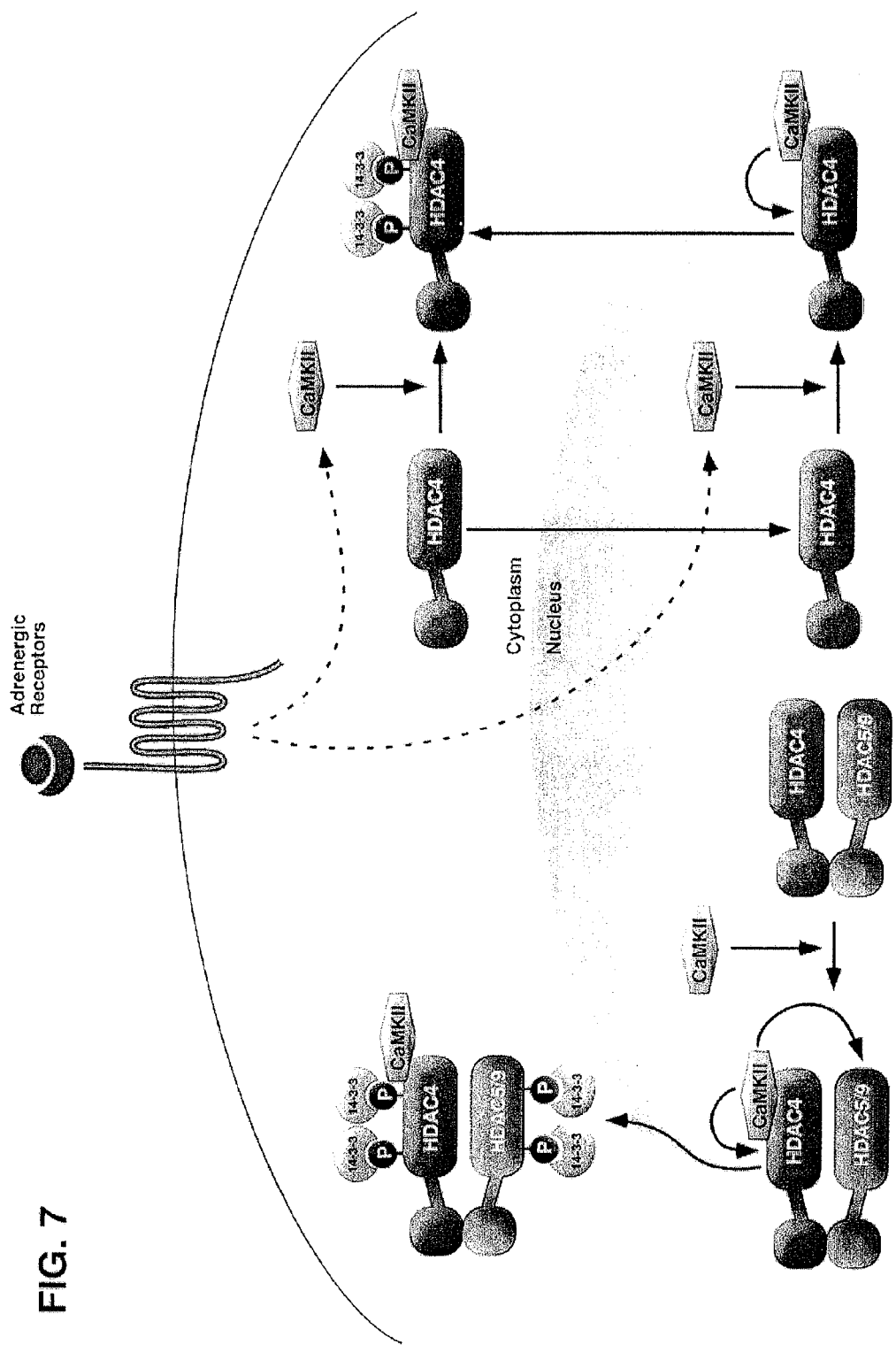
FIG. 7—A model of CaMKII and HDAC4-dependent nuclear export of a class II HDAC complex. Adrenergic stimulation activates CaMKII. Activated CaMKII interacts site-specific with HDAC4 which results in phosphorylation of HDAC4 and 14-3-3 protein-mediated nuclear export. While CaMKII does not bind to HDAC5 or 9, it localizes in a close proximity after binding to the dimerization partner HDAC4 which enables CaMKII now to phosphorylate HDAC5 and 9. 14-3-3 protein binding to either HDAC4 or HDAC5/9 is sufficient to induce nuclear export of the dimerized HDAC complex.

Consistently, GAL4-HDAC4 mutants, containing alanine, phenylalanine, lysine or leucine in place of Arg-601, were markedly impaired in their ability to bind 14-3-3 in response to CaMKIIδb-T287D (FIG. 5E), whereas the basal 14-3-3 binding activity of these HDAC4 mutants was comparable to that of wild-type HDAC4 (not shown). While HDAC4 R601A and R601K showed a slight CaMKII-induced increase in 14-3-3 binding (below 2-fold), mutations of Arg-601 to non-polar hydrophobic amino acids (phenylalanine or leucine) prevented 14-3-3 binding in response to CaMKII completely. Again, these CaMKII non-responsive mutants were not affected in their ability to bind 14-3-3 in response to CaMKI (not shown). The inventors conclude that HDAC4 contains a unique domain that selectively binds to activated CaMKII. This domain is located between the CaMKII phosphorylation sites Ser-467 and Ser-632. The disruption of this binding domain by mutation of the critical residue Arg-601 prevents phosphorylation of HDAC4 by CaMKII but not by CaMKI.

HDAC4 heterodimerizes and co-exports HDAC5 and MITR in response to CaMKII. Although the data demonstrate that CaMKII selectively regulates nucleocytoplasmic shuttling of HDAC4 but not of other class II HDACs, it has also been reported that CaMKII inhibitors block nuclear export of HDAC5 in response to depolarization of cerebellar granule neurons40. This disparity might be explained if CaMKII activated other downstream kinases that phosphorylate HDAC5. However, Kirsh et al. (2002) reported that HDAC4 possesses the ability to self-aggregate at its N-terminus. Since this domain, which is glutamine-rich, is highly conserved between HDAC4, 5 and 9, the inventors asked if these HDACs were able to heterodimerize and if so whether this might allow HDAC5 or 9 to respond indirectly to CaMKII signaling. Expression of HDAC4 together with HDAC5 or MITR resulted in co-localization of these proteins (FIG. 6A). In response to CaMKIIδb-T287D, not only was HDAC4 exported from the nucleus but also HDAC5 and MITR. This effect on MITR was especially intriguing because MITR lacks an NES and even remains localized exclusively to the nucleus when phosphorylated by CaMKI. The observation that MITR co-localized with HDAC4 to the cytosol in response to CaMKII thus suggested a co-shuttling mechanism.

Using co-immunoprecipitation assays, the inventors confirmed that HDAC4 self-associates and heterodimerizes with HDAC5 (FIG. 6B and FIG. 6C) and MITR, but not HDAC7 (data not shown). A mutant form of HDAC4 lacking the first 200 amino acids failed to induce the redistribution of HDAC5 to the cytosol in the presence of CaMKIIδb-T287D, confirming that this region of HDAC4 is critical for co-shuttling (FIG. 6D).

The inventors postulated two potential explanations for the ability of HDAC4 to confer CaMKII responsiveness to HDAC5 and 9: (1) CaMKII could specifically phosphorylate only HDAC4, which might then act as a chaperone to export HDAC5 without HDAC5 itself being phosphorylated; or (2) HDAC4 could serve as a docking site for CaMKII, bringing the kinase into close proximity to HDAC5 and allowing phosphorylation of HDAC5. To distinguish between these possibilities, the inventors tested whether a HDAC5 mutant lacking the signal-responsive phosphorylation sites (S259/498A; S/A) could translocate from the nucleus to the cytoplasm in the presence of HDAC4. Conversely, the inventors tested whether HDAC4-S/A could translocate to the cytoplasm with wild-type HDAC5. Remarkably, HDAC4 co-shuttled the signal resistant HDAC5-S/A mutant to the cytosol in response to CaMKIIδb-T287D, confirming the passive mechanism (mechanism 1) (FIG. 6E). Moreover, HDAC4-S/A was also exported in the presence of wild-type HDAC5, consistent with mechanism 2 above (FIG. 6F). The inventors conclude that HDAC4 must provide a docking site for CaMKII, but once docked, CaMKII can phosphorylate either HDAC4 or its dimerization partner, in this case HDAC5, with consequent nuclear export of the multiprotein HDAC:CaMKII complex.

B. Example 2

1. Materials and Methods

COS Transfection, plating, culture maintenance and test compound dosing procedures. COS cells are trypsinized cell density counted with a hemocytometer. COS cells are then diluted in a laminar flow hood to 40,000 cells/mL in HyQ DME/High Modified culture media (Fisher) supplemented with 10% FBS and 1:100 P/S/G. A total of 0.768 million cells are required per 384-well plate, however, it is important to include an extra 1.536 million cells in the calculation of cells needed for the screen in order to allow for the cell suspension that is lost during the priming the Bio-Tek® μFill™. The total amount of DNA needed is calculated (5 μg of DNA per million cells). The total amount of DNA consists of half HDAC4-GFP and half CAMKIIδB T287D. The amount of FuGENE 6 needed is then calculated (6 μL FuGENE 6 per μg DNA). The FuGENE 6 is diluted in an amount of DMEM equal to 33.3× the amount of FuGENE 6 used and incubated for 5 min at room temp. The FuGENE 6/DMEM is added in solution to another tube containing the DNA and incubate for 15 min at RT. The COS cells are then combined with the FuGENE 6/DMEM/DNA mixture.

COS cells are dispensed at 2,000 cells/well using the Bio-Tek® μFill™ liquid dispenser in the laminar flow hood into gel-coated Costar 3712 384-well plates. Cells are incubated at 37° C. in 5% $CO_2$/100% humidity for 44-48 hours, then the media is aspirated and the cells are washed once with DPBS, 1×w/Ca & Mg using the Bio-Tek® ELx405™ Select in the laminar flow hood. The cells are then given an immediate dispensal of 90 μL of HyQ DME/High Modified culture media supplemented with 1:100 P/S/G using the μFill in the laminar flow hood. Compound dosing is performed using the Biomek® FX and the cells are incubated at 37° C. in 5% $CO_2$/100% humidity for 3 hrs after dosing with test compounds.

Fixation Procedure. Media is aspirated from the COS cell plates and washed twice with 100 μL/well 1×PBS using the Bio-Tek® ELx405™ HT. Cells are fixed by adding 50 μL/well 5% paraformaldehyde using the Bio-Tek® μFill™. Then the plates are incubated at room temperature for 30 minutes. The paraformaldehyde is aspirated from the plates and the plates are washed twice with 100 μL/well 1×PBS+ 0.05% Tween-20, using the Bio-Tek® ELx405™ HT. Then to each well is added 50 μL/well of 1×PBS+0.05% Tween-20+2 μg/mL Hoechst using the Bio-Tek® μFill™. The plates are incubated at room temperature for 60 minutes. The Hoechst solution is then aspirated from the plates and wash twice with 100 μL/well 1×PBS+0.05% Tween-20, using the Bio-Tek® ELx405™HT. Next add 50 μL/well of 1×PBS+0.05% Tween-20, using the Bio-Tek® μFill™, and then seal the plates with clear adhesive film and read on the Cellomics plate reader.

2. Results

Quantification of subcellular localization of HDAC4-GFP. To determine the performance of the cellomics based CaMKII assay, COS cell were treated with DNA/fugene complexes as described in the materials and methods. Two different transfection mixes were prepared both of which contained HDAC4-GFP, while one of the mixes included CaMKII expressing plasmid DNA and the other empty vector DNA. The cell/DNA mixture was then palted on 384-well plates at 2000 cells/well. Plated cells were incubated at 37° C., 5% CO2 for 48 hrs. Following incubation the cells were fixed and imaged on the cellomics array scanner using the nuclear translocation protocol. The results shown in FIG. 11 indicate that there is a large difference in the nuclear-cytoplasmic fluorecense intensity index (Nuc-Cyto) between the two transfection conditions. The no-CaMKII transfection has high values for the nuclear-cytoplasmic fluorecense intensity index, consistent with nuclear localization of the HDAC4-GFP chimera, while the CaMKII transfections has low value for that index, consistent with cytoplasmic localization of the HDAC4-GFP chimera. The signal to background (S/B=(Nuc-Cyto for CaMKII)/(Nuc-Cyto for no CaMKII control)) is about 11-fold if the media of the cells was switched to serum-free media following overnight incubation and about 8-fold if the cells were continued cultured in serum containing media. The signal to noise (S/N=((Nuc-Cyto for CaMKII)-(Nuc-Cyto for no CaMKII control))/(standard deviation(Nuc-Cyto for CaMKII))) is about 21 and 15 for the for the two transfection conditions. Finally, the z values (z=1-(((3*stdev(Nuc-Cyto for CaMKII)+3*(Nuc-Cyto for no CaMKII control))/(|(Nuc-Cyto for CaMKII)-(Nuc-Cyto for no CaMKII control)|))) are 0.4 and 0.3 for the two transfection conditions. These parameters indicate that this assay well behaved for screening.

Figure 12:
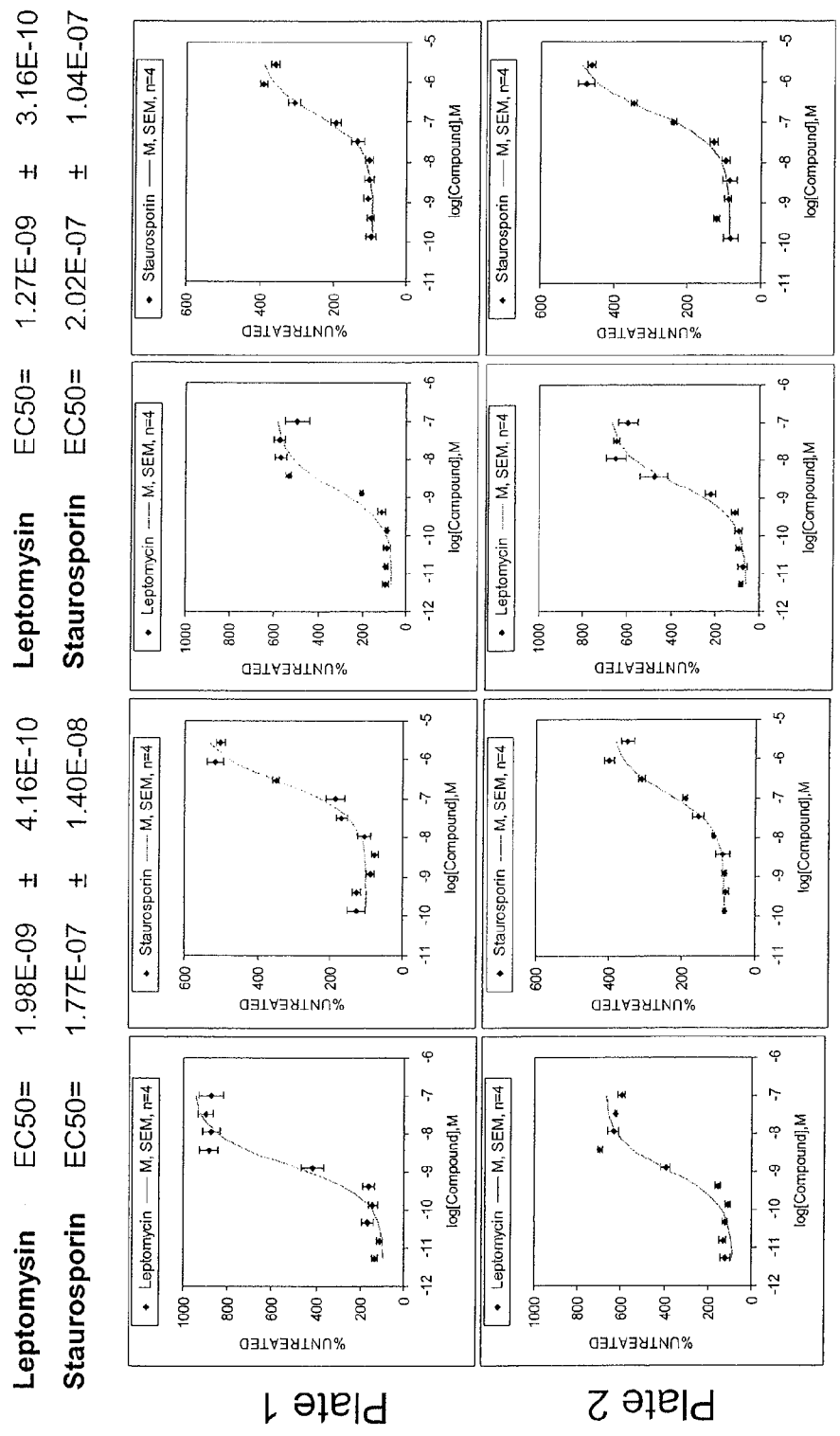
FIG. 12—Cellomics assay performance. Assays were set as described in previous figure with the exception that all cells were transfected with HDAC4-GFp and activated CaMKII. Following overnight incubation the cells were dosed with a dose range of Leptomycin and Staurosporine as indicated. Data were expressed as present of vehicle treated controls and were fitted to a monophasic sigmoidal dose response. Form fitted data we calculated EC50 values, shown as average for each plate along with standard deviations. This experiment was repeated two different days as shown to check variability.

Dose response analysis. To test the assay in a dose response format, cells were transfected with HDAC4-GFP and CaMKII plasmids as described above. Following overnight incubation the cells were dosed with a concentration range of leptomycin and staurosporine. Leptomycin is a general inhibitor of nuclear export while staurosporine is a promiscuous inhibitor of Ser/Thr kinases. Cells were fixed at 48 hrs and analyzed on the cellomics instrument. The results shown in FIG. 12 clearly show that assay is sensitive to the presence of these inhibitors showing smooth dose response curves. These curves can be fitted to standard pharmacological models and extract $EC_{50}$ values as shown in FIG. 12.

Figure 13:
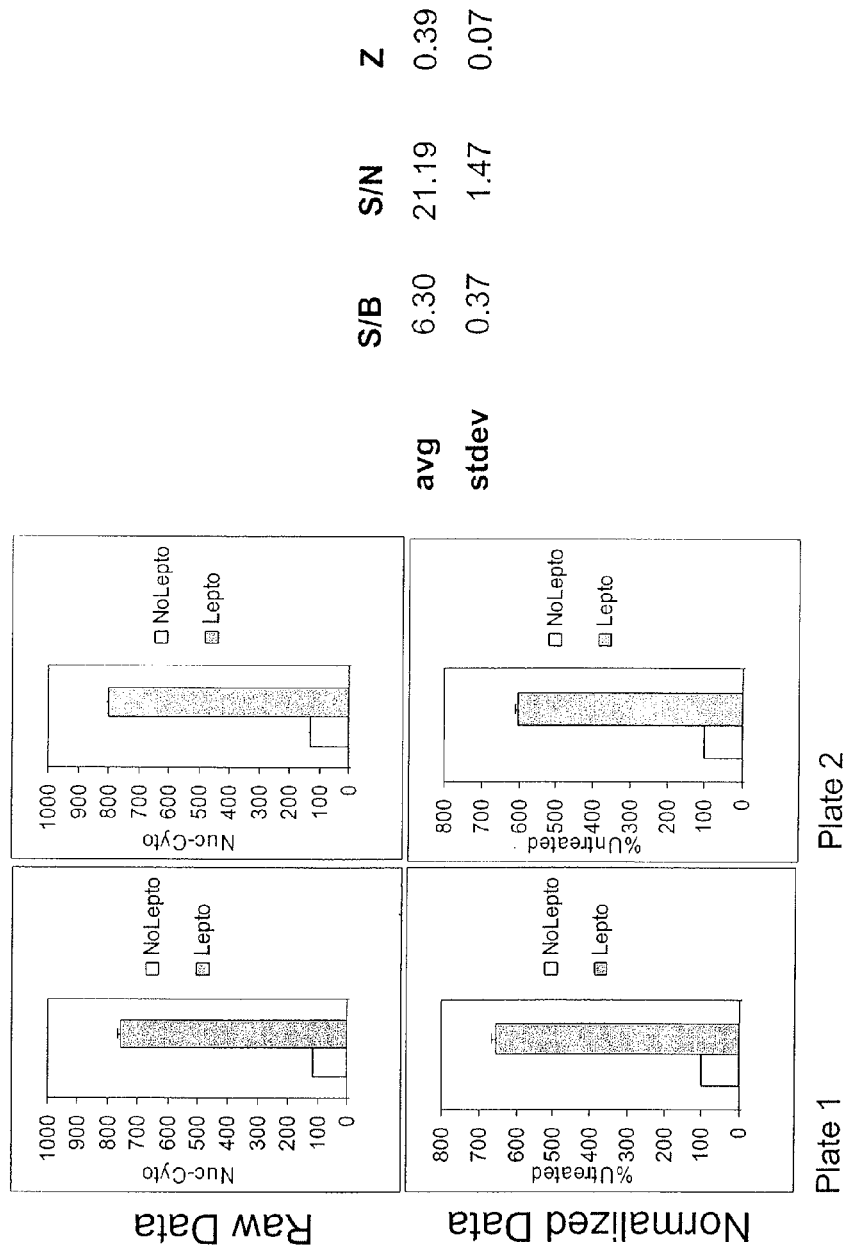
FIG. 13—Cellomics assay performance. Cell were plated on 384 well plates and transfected with HDAC4-GFP and activated CaMKII plasmid as described. Following overnight incubation half of the wells on each plate were treated with leptomycing simulating a positive hit in the assay. Cells were then treated and data were analyzed as described. Symbols are as described in previous figures.

Assay behavior under screening conditions. For screening, only one transfection mix is necessary, the one containing CaMKII. To test the assay behavior under such conditions, cells were transfected with HDAC4-GFP and CaMKII plasmid and plated as described above. Following overnight incubation, half of the wells of the plate were treated with either leptomycin of staurosporine. At 48 hrs post-transfection the cells were fixed and analyzed as above (FIG. 11). As seen in FIG. 13, this assay again showed good statistics with S/B, S/N and z values of approximately 6, 21 and 0.4, respectively.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. REFERENCES

The following references, to the extent that they provide exemplary procedural or other details supplementary to those set forth herein, are specifically incorporated herein by reference:

Aus. Pat. No. 6,794,700.
Aus. Pat. No. 9,013,101.
Aus. Pat. No. 9,013,201.
Aus. Pat. No. 9,013,401.
Benjamin & Schneider, *J. Clin. Invest.*, 115:495-9, 2005.
Bright, *Proc. 17th ACVIM*, Chicago, 134-135, 1999.
Brown, *Compendium Cont. Educ. Practicing Vetn.*, 21:752-763, 1999.
Butler et al., *Cancer Res.*, 60:5165-5170, 2000.
Butler et al., *Clin. Cancer Res.*, 7:962-970, 2001.
Chang et al., *Mol. Cell. Biol.*, 24:8467-76, 2004.
Chien, K. R., *Cell*, 98:555-8, 1999.
Coffey et al., *Cancer Res.*, 61:3591-3594, 2001.
Colomer et al., *Mol. Endocrinol.*, 17:183-92, 2003.
Colomer & Means, *Mol. Endocrinol.*, 14:1125-36, 2000.
Cooke et al., *J. Vet. Intern. Med.*, 12:123, 1998.
Davis et al., *J. Biol. Chem.*, 278:20047-58, 2003.
Dequiedt et al., *J. Exp. Med.*, 201:793-804, 2005.
Dorn et al., *Circ. Res.*, 92:1171-5, 2003.
Dresdale et al., *Am. J. Med.*, 11(6): 686-705, 1951.
Edmondson et al., *Development*, 120:1251-63, 1994.
Elliott and Barber, *J. Small Animal Practice*, vol. 39:78, 1998.
Eur. Pat. No. 0089167
Eur. Pat. No. 1,123,111.
Eur. Pat. No, 1,170,008.
Eur. Pat. No. 1,173,562.
Eur. Pat. No. 1,174,438.
Eur. Pat. No. 1,208,086.
Eur. Pat. No. 1,233,958.
Eur. Pat. No. 1,548,026
Finco et al., *J. Vet. Intern. Med.*, 13:516-528, 1999.
Frey & Olson, *Annu. Rev. Physiol.*, 65:45-79, 2003.
Furumai et al., *Cancer Res.*, 62:4916-21, 2002.
Gao et al., *J. Biol. Chem.*, 277:25748-55, 2002.
Gottlicher et al., *EMBO J.*, 20:6969-78, 2001.
Grozinger et al., *Proc. Natl. Acad. Sci. USA*, 96:4868-4873, 1999.
Gusterson et al., *J. Biol. Chem.*, 278:6838-47, 2003.
Han et al., *Cancer Research*, 60:6068-6074, 2000.
Haraldsson et al., *Anesth. Analg.*, 93(6): 1439-1445, 2001.
Haribabu et al., *EMBO Journal* 14:3679-86, 1995.
Henik et al., *J. Am. Animal Hosp. Assoc.*, 33(3):226-234, 1997.
Hinnebusch et al., *J. Nutr.*, 132:1012-7, 2002.
Hoch et al., *Circ. Res.*, 84:713-21, 1999.
Hoffmann et al., *Bioconjugate Chem.*, 12:51-55, 2001.
Igaku, *Experimental Medicine*, 13:35-42, 1995.
Japanese Patent Application No. 2001/348340.
Jung, *Curr. Med. Chem.*, 8:1505-11, 2001.
Jung et al., *J. Med. Chem.*, 42:4669-4679, 1999.
Jung et al., *Med. Chem. Lett.*, 7:1655-1658, 1997.
Kao et al., *J. Biol. Chem.*, 276:47496-507, 2001.
Kao et al., *Genes Dev.*, 14:55-66, 2000.
Kato et al., *Circ. Res.*, 87:937-45, 2000.
Katoh et al., *J. Biol. Chem.*, 273:1511-18, 1998.
Kim et al., *Oncogene*, 18:2461-2470, 1999.
Kirsh et al., *Embo. J.*, 21:2682-91, 2002.
Kitazono et al., *J. Clinical Endoc. Metabol.*, 86(7):3430-3435, 2001.
Komastsu et al., *Cancer Res.*, 61:4459-4466, 2001.
Kramer et al., *Trends in Endoc. Metabolism*, 12)7):294-300, 2001.
Lu et al., *Proc. Natl. Acad. Sci. USA*, 97:4070-4075, 2000.
Mai et al., *J. Med. Chem.*, 45:1778-1784, 2002.
Marks et al., *J. Natl. Cancer Inst.*, 92(15):1210-1216, 2000.
Marks et al., *Clin. Cancer Res.*, 7:759-760, 2001.
Massa et al., *J. Med. Chem.*, 44:2069-2072, 2001.

The Merck Index, O'Neil et al., ed., 16th Ed., 2001.
McKinsey & Olson, *Trends Genet.*, 20:206-13, 2004.
McKinsey and Olson, *Annu. Rev. Physiol.*, 65:45-79, 2003.
McKinsey et al., *Mol. Cell. Biol.*, 21:6312-21, 2001.
McKinsey et al., *Proc. Natl. Acad. Sci. USA*, 97:14400-14405, 2000a.
McKinsey et al., *Nature*, 408:106-111, 2000b.
Michell, *Vet. Annual*, 35:159, 1995.
Miska et al., *Embo. J.*, 18:5099-107, 1999.
Miyano et al., *J. Biol. Chem.*, 267:1198-203, 1992.
Molkentin et al., *Cell*, 93:215-228, 1998.
Naya et al., *Development*, 126:2045-52, 1999.
Oudiz et al., at www.emedicine.com/med/topic1962.htm, visited May 25, 2004.
Parra et al., *J. Biol. Chem.*, 280:13762-70, 2005.
Passier et al., *J. Clin. Invest.*, 105:1395-406, 2000.
PCT Application No. WO 84/03564.
PCT Application No. WO 01/14581.
PCT Application No. WO 01/18045.
PCT Application No. WO 01/38322.
PCT Application No. WO 01/42437.
PCT Application No. WO 01/70675.
PCT Application No. WO 02/26696.
PCT Application No. WO 02/26703.
PCT Application No. WO 02/30879.
PCT Application No. WO 02/46129.
PCT Application No. WO 02/46144.
PCT Application No. WO 02/50285.
PCT Application No. WO 02/51842.
PCT Application No. WO 04/13130
PCT Application No. WO 04/82638
PCT Application No. WO 04/87693
PCT Application No. WO 04/92115
PCT Application No. WO 04/112763
PCT Application No. WO 04/113336
PCT Application No. WO 05/00282
PCT Application No. WO 05/14588
PCT Application No. WO 05/19174
PCT Application No. WO 05/30704
PCT Application No. WO 05/30705
PCT Application No. WO 05/40101
PCT Application No. WO 05/40161
PCT Application No. WO 05/51901
PCT Application No. WO 05/58803
PCT Application No. WO 05/65681
PCT Application No. WO 05/66151
PCT Application No. WO 05/71079
PCT Application No. WO 05/75466
Pearce et al., *New Horizons*, 4:123, 1996.
Ramirez et al., *J. Biol. Chem.*, 272:31203-8, 1997.
Reams et al., *Am. J. Kidney Diseases*, 6:446, 1987
Remington's Pharmaceutical Sciences, 15th ed., pages 1035-1038 and 1570-1580, Mack Publishing Company, Easton, Pa., 1980.
Roth et al., *Annu. Rev. Biochem.*, 70:81-120, 2001.
Saunders et al., *Cancer Res.*, 59-399-409, 1999.
Schermuly et al., *Am. J. Respir. Crit. Care. Med.*, 164(9):1694-700, 2001.
Schoen, F. J. "Blood Vessels." Robbins Pathologic Basis of Disease, eds. R. S. Cotran V. Kumar, and F. J. Schoen, Philadelphia, W. B. Saunders Company, 467-516, 1994.
Seikagaku, *Biochemistry*, 65:537-552, 1993.
Snyder, *J. Vet. Intern. Med.*, 12:157, 1998.
Su et al., *Cancer Res.*, 60:3137-3142, 2000.
Takahashi et al., *Antibiotics*, 49:453, 1996.
Taunton et al., *Science*, 272:371, 1996.
Thiagalingham et al., *Ann. N.Y. Acad. Sci.*, 983:84-100, 2003.
Tong et al., *Nucleic Acids Res.*, 30:1114-23, 2002.
Uemura et al., *Biochem. Biophys. Res. Commun.*, 249:355-60, 1998.
U.S. Pat. No. 6,706,886
U.S. Pat. No. 6,521,647
U.S. Pat. No. 6,201,165
U.S. application Ser. No. 10/801,985
United States App. 2002/61860.
United States App. 2002/65282.
United States App. 2002/103192.
Van den Wyngaert et al., *FEBS Lett.*, 478:77-83, 2000.
Vega et al., *Mol. Cell. Biol.*, 24:8374-85, 2004.
Verdin et al., *Trends Genet.*, 19:286-93, 2003.
Vigushin et al., *Anticancer Drugs*, 13:1-13, 2002.
Vigushin et al., *Cancer Res.*, 5(Suppl), 1999.
Vigushin et al., *Clinical Cancer Res.*, 7:971-976, 2001.
Workman and Kingston, *Annu. Rev. Biochem.*, 67:545-579, 1998.
Yamano et al., Amer. Soc. Gene Ther., 2000.
Yanazume et al., *Mol. Cell. Biol.*, 23:3593-606, 2003.
Young et al., Handbook of Applied Therapeutics, 7.1-7.12 and 9.1-9.10, 1989.
Zhang et al., *Cell*, 110:479-88, 2002.
Zhang et al., *Circ. Res.*, 92:912-9, 2003.
Zhang et al., *Nat. Med.*, 2005.
Zhou et al., *Proc. Natl. Acad. Sci.*, 98:10572-10577, 2001.

What is claimed is:

1. A method of treating cardiac hypertrophy, heart failure, dilated cardiomyopathy, or arrhythmias comprising:
   (a) identifying a subject suffering from or at risk of developing cardiac hypertrophy, heart failure, dilated cardiomyopathy, or arrhythmias; and
   (b) administering to said patient an Histone Deacetylase (HDAC) 4 peptide of 5 to 25 consecutive residues of HDAC4 and comprising the docking site to Calcium/Calmodulin Kinase II (CaMKII), or a CaMKII peptide of 5 to 25 consecutive residues of CaMKII and comprising the docking site to HDAC4, that inhibits the interaction between HDAC4 and CaMKII.

2. The method of claim 1, wherein said peptide consists of only the HDAC4 docking site to CaMKII.

3. The method of claim 1, where said CaMKII peptide is a peptide of CaMKII α comprising the docking site to HDAC4.

4. The method of claim 1, wherein said peptide consists of only the CaMKII docking site to HDAC4.

5. The method of claim 1, wherein step (b) comprises administering to said patient an HDAC4 peptide of 5 to 25 consecutive residues of HDAC4 and comprising the docking site to CaMKII.

6. The method of claim 1, wherein step (b) comprises administering to said patient a CaMKII peptide of 5 to 25 consecutive residues of CaMKII and comprising the docking site to HDAC4.

7. The method of claim 1, where said CaMKII peptide is a peptide of CaMKII-β comprising the docking site to HDAC4.

8. The method of claim 1, where said CaMKII peptide is a peptide of CaMKII-γ comprising the docking site to HDAC4.

9. The method of claim 1, where said CaMKII peptide is a peptide of CaMKII-δ comprising the docking site to HDAC4.

* * * * *

UNITED STATES PATENT AND TRADEMARK OFFICE
CERTIFICATE OF CORRECTION

PATENT NO. : 7,863,414 B2  
APPLICATION NO. : 11/560950  
DATED : January 4, 2011  
INVENTOR(S) : Johannes Backs et al.

Page 1 of 1

It is certified that error appears in the above-identified patent and that said Letters Patent is hereby corrected as shown below:

In title page, item (73) Assignees, column 1, lines 1-2, delete "The Board of Regents of the University of Texas Systems, Austin, TX (US)" and insert --The Board of Regents of the University of Texas System, Austin, TX (US)-- therefor.

In column 1, lines 9-11, delete
"The government owns rights in this application purusant to federal funding from the National Institutes of Health under Grant No. R01 HL53351-06." and insert
--This invention was made with government support under grant number R01 HL53351-06 awarded by the National Institutes of Health. The government has certain rights in the invention.--

Signed and Sealed this  
Tenth Day of May, 2011

David J. Kappos  
*Director of the United States Patent and Trademark Office*